United States Patent
Fukuda et al.

(10) Patent No.: US 8,234,941 B2
(45) Date of Patent: Aug. 7, 2012

(54) SPECIMEN ANALYZING APPARATUS AND SPECIMEN ANALYZING METHOD

(75) Inventors: Kazuya Fukuda, Kobe (JP); Hiroki Koike, Kobe (JP); Hironori Katsumi, Kobe (JP); Takashi Yamato, Kakogawa (JP); Masayuki Ikeda, Kobe (JP); Tsuyoshi Fukuzaki, Akashi (JP); Daisuke Nakano, Kobe (JP); Masanori Imazu, Takasago (JP); Nobuhiro Kitagawa, Akashi (JP)

(73) Assignee: Sysmex Corporation, Kobe (JP)

( * ) Notice: Subject to any disclaimer, the term of this patent is extended or adjusted under 35 U.S.C. 154(b) by 463 days.

(21) Appl. No.: 12/607,739

(22) Filed: Oct. 28, 2009

(65) Prior Publication Data
US 2010/0107744 A1 May 6, 2010

(30) Foreign Application Priority Data

Oct. 31, 2008 (JP) ................................ 2008-281585
Mar. 18, 2009 (JP) ................................ 2009-065641

(51) Int. Cl.
*G01N 35/00* (2006.01)
*G01N 35/02* (2006.01)
*G01N 35/10* (2006.01)

(52) U.S. Cl. ............... 73/864.81; 73/863.01; 73/863.02; 73/864.21; 422/67

(58) Field of Classification Search ................. 73/64.56, 73/863–863.02, 864.21, 864.24–864.25, 73/864.81; 422/63–65, 67, 509; 436/43, 436/45, 47, 50, 54, 180
See application file for complete search history.

(56) References Cited

U.S. PATENT DOCUMENTS

| | | | |
|---|---|---|---|
| 5,587,129 A | 12/1996 | Kurosaki et al. | |
| 2006/0237312 A1* | 10/2006 | West et al. | 204/401 |
| 2007/0202608 A1* | 8/2007 | Uffenheimer et al. | 436/180 |
| 2007/0231206 A1* | 10/2007 | Nagai et al. | 422/63 |
| 2009/0035873 A1* | 2/2009 | Shibata | 422/63 X |
| 2009/0104078 A1* | 4/2009 | Seguin | 422/99 |
| 2010/0093097 A1* | 4/2010 | Kawamura | 436/43 |

FOREIGN PATENT DOCUMENTS
EP     0210014 A2 * 1/1987
* cited by examiner

*Primary Examiner* — Thomas P Noland
(74) *Attorney, Agent, or Firm* — Sughrue Mion, PLLC

(57) ABSTRACT

A specimen analyzing apparatus comprising: a detector for detecting component information regarding a component in a specimen contained in each of analyzing containers, the analyzing containers comprising first and second analyzing containers; an analyzing part for analyzing the component information detected by the detector; a transporting device for transporting specimen containers each containing a specimen, the specimen containers comprising first and second specimen containers; an operation mode selector for selecting one of a first operation mode and a second operation mode; a first supplying device for supplying the specimen of a first amount; a second supplying device for supplying the specimen of a second amount grater than the first amount; and a supply controller for controlling the first and second supplying devices in accordance with an operation mode selected by the operation mode selector, is disclosed. A specimen analyzing method is also disclosed.

19 Claims, 17 Drawing Sheets

Fig. 14

| RACK IDENTIFICATION INFORMATION | CONTAINER POSITION | SPECIMEN IDENTIFICATION INFORMATION | MEASUREMENT ITEM | RE-EXAMINATION SCHEDULE |
|---|---|---|---|---|
| R001 | 1 | C001 | Fbg | NOT SCHEDULED |
| R001 | 2 | C002 | PT | SCHEDULED |
| R001 | 3 | C003 | PT | SCHEDULED |
| ... | ... | ... | ... | ... |

SPECIMEN ANALYZING APPARATUS AND SPECIMEN ANALYZING METHOD

FIELD OF THE INVENTION

The present invention relates to a specimen analyzing apparatus, and particularly to a specimen analyzing apparatus and a specimen analyzing method, the specimen analyzing apparatus having a pipette for dispensing a specimen contained in a specimen container having been transported by a transporting device, into a cuvette that is disposed within the specimen analyzing apparatus.

BACKGROUND

Conventionally, there is a known specimen analyzing apparatus that is capable of: first, dispensing a specimen, which is contained in a specimen container having been transported by a transporting device to an aspirating position, into a cuvette disposed within the specimen analyzing apparatus; thereafter, dispensing a part of the specimen previously dispensed into the cuvette, into another cuvette within the specimen analyzing apparatus; and then optically measuring the specimen in this another cuvette.

For example, U.S. Pat. No. 5,587,129 discloses such a specimen analyzing apparatus as above, which includes: a transporting device for transporting a rack holding sample containers, each of which contains a specimen; a first turntable for holding stock containers; first dispensing means configured to dispense, using a first pipette, a specimen from a sample container into a stock container held by the first turntable; a second turntable for holding analyzing containers; second dispensing means configured to dispense, using a second pipette, a part of the specimen having been dispensed into the stock container held by the first turntable, into an analyzing container held by the second turntable; analyzing stages for measuring light intensity of scattered light or transmitted light by emitting light to specimens in analyzing containers; a first chucking finger, capable of holding a stock container or analyzing container, for supplying these containers to the first turntable and the second turntable; and a second chucking finger for transferring an analyzing container held by the second turntable to an analyzing stage.

In the specimen analyzing apparatus described in U.S. Pat. No. 5,587,129, a specimen is first dispensed, by the first dispensing means, from a sample container into a stock container held by the first turntable, and the second dispensing means dispenses a part of the specimen contained in the stock container, into an analyzing container held by the second turntable. In this manner, the specimen partially remains in the stock container held by the first turntable. Then, when the specimen needs to be examined again, the specimen analyzing apparatus described in U.S. Pat. No. 5,587,129 automatically searches the first turntable and finds the stock container that contains the partial specimen, and the second dispensing means dispenses the specimen in the stock container into another analyzing container held by the second turntable. Then, the specimen is analyzed again on an analyzing stage.

As described above, in the technique disclosed in U.S. Pat. No. 5,587,129, a sufficient amount of specimen for examination and re-examination thereof is dispensed from a sample container into a stock container by the first dispensing means, so that re-examination can be performed promptly when requested. A necessary amount of specimen for examination is dispensed from the stock container into an analyzing container by the second dispensing means. This technique is excellent in terms of being able to perform re-examination very readily.

However, U.S. Pat. No. 5,587,129 does not disclose, for example, how to meet a need regarding examination as described below. For instance, some examination items do not require re-examination in some examination facilities. Accordingly, there is a need for speedily performing examinations while securing precision thereof even in the case where consecutive measurement is performed to a large number of specimens which include specimens to be examined for examination items that require re-examinations, and specimens to be examined only for examination items that do not require re-examinations, are mixed.

Further, the sample containers used herein are those having a cap attached thereto, such as vacuum blood collection tubes, and those without a cap. In order to precisely aspirate a predetermined amount of specimen from a sample container having a cap attached thereto, it is necessary to perform a complex operation, for example, releasing pressure from the inside of the sample container and then aspirating the specimen, which is time consuming. Thus, there is a need for speedily performing examinations even if containers having a cap attached thereto and containers without a cap are mixed. However, U.S. Pat. No. 5,587,129 does not disclose how to meet such a need regarding examination.

SUMMARY

The scope of the present invention is defined solely by the appended claims, and is not affected to any degree by the statements within this summary.

A first aspect of the present invention is a specimen analyzing apparatus comprising: a detector for detecting component information regarding a component in a specimen contained in each of analyzing containers, the analyzing containers comprising first and second analyzing containers; an analyzing part for analyzing the component information detected by the detector; a transporting device for transporting specimen containers each containing a specimen, the specimen containers comprising first and second specimen containers; an operation mode selector for selecting one of a first operation mode for supplying the specimen of a first amount, which is a necessary amount for analyzing the specimen, from the first specimen container to the first analyzing container, and a second operation mode for supplying the specimen of a second amount greater than the first amount from the second specimen container to a reserve container and for supplying the specimen of the first amount from the reserve container to the second analyzing container; a first supplying device for supplying the specimen of the first amount; a second supplying device for supplying the specimen of the second amount; and a supply controller for controlling the first and second supplying devices in accordance with an operation mode selected by the operation mode selector.

A second aspect of the present invention is a specimen analyzing apparatus comprising: a detector for detecting component information regarding a component in a specimen contained in each of analyzing containers, the analyzing containers comprising first and second analyzing containers; an information analyzing device for analyzing the component information detected by the detector; a first supplying device for supplying the specimen of a first amount that is a necessary amount for the analyzing by the information analyzing device; a second supplying device for supplying the specimen of a second amount that is greater than the first amount; a transporting device for transporting specimen containers each containing a specimen, the specimen containers comprising first and second specimen containers; and a control device for performing a process comprising: (a) selecting one of a first operation mode for supplying the specimen of the first amount from the first specimen container to the first analyzing container, and a second operation mode for supplying the specimen of the second amount from the second specimen container to a reserve container and for supplying the specimen of the first amount from the reserve container to the second analyzing container; and (b) controlling the first and second supplying devices in accordance with the selected operation mode.

A third aspect of the present invention is a specimen analyzing method comprising steps of: (a) transporting specimen containers each containing a specimen, the specimen containers comprising first and second specimen containers; (b) selecting one of a first operation mode and a second operation mode; (c) supplying the specimen of a first amount which is a necessary amount for analyzing the specimen, from the first specimen container to a first analyzing container when the first operation mode has been selected; (d) supplying the specimen of a second amount which is greater than the first amount, from the second specimen container to a reserve container, and supplying the specimen of the first amount from the reserve container to a second analyzing container when the second operation mode has been selected; (e) detecting component information regarding a component contained in the specimen having been supplied to the first or second analyzing container; and (f) analyzing the component information.

BRIEF DESCRIPTION OF THE DRAWINGS

FIG. 14 shows an example of a measurement order according to the embodiment of the present invention;

DETAILED DESCRIPTION OF THE EMBODIMENT

Hereinafter, a preferred embodiment of the present invention will be described with reference to the drawings. A specimen analyzing apparatus according to the present embodiment is a blood coagulation measuring apparatus for optically measuring and analyzing a specimen by using a coagulation time method, synthetic substrate method, immunonephelometry, and a platelet aggregation method. The blood coagulation measuring apparatus is configured to consecutively measure and analyze a plurality of specimens for which a measurement order is registered.

Figure 1:
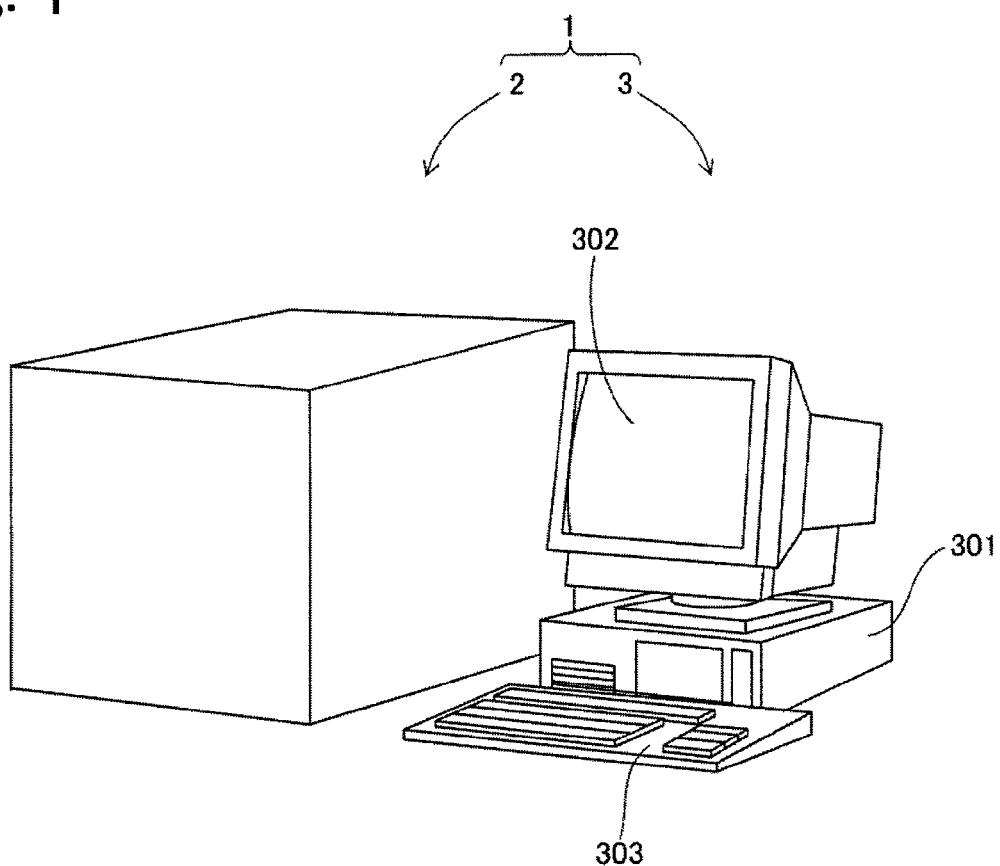
FIG. 1 is a perspective view showing an external view of a specimen analyzing apparatus 1 according to an embodiment of the present invention.

FIG. 1 is a perspective view showing an external view of a specimen analyzing apparatus 1. As shown in FIG. 1, the specimen analyzing apparatus 1 includes: a measurement apparatus 2 for optically measuring components contained in specimens (blood); and an information processing apparatus 3 for analyzing results of the measurement performed by the measurement apparatus 2.

Figure 2:
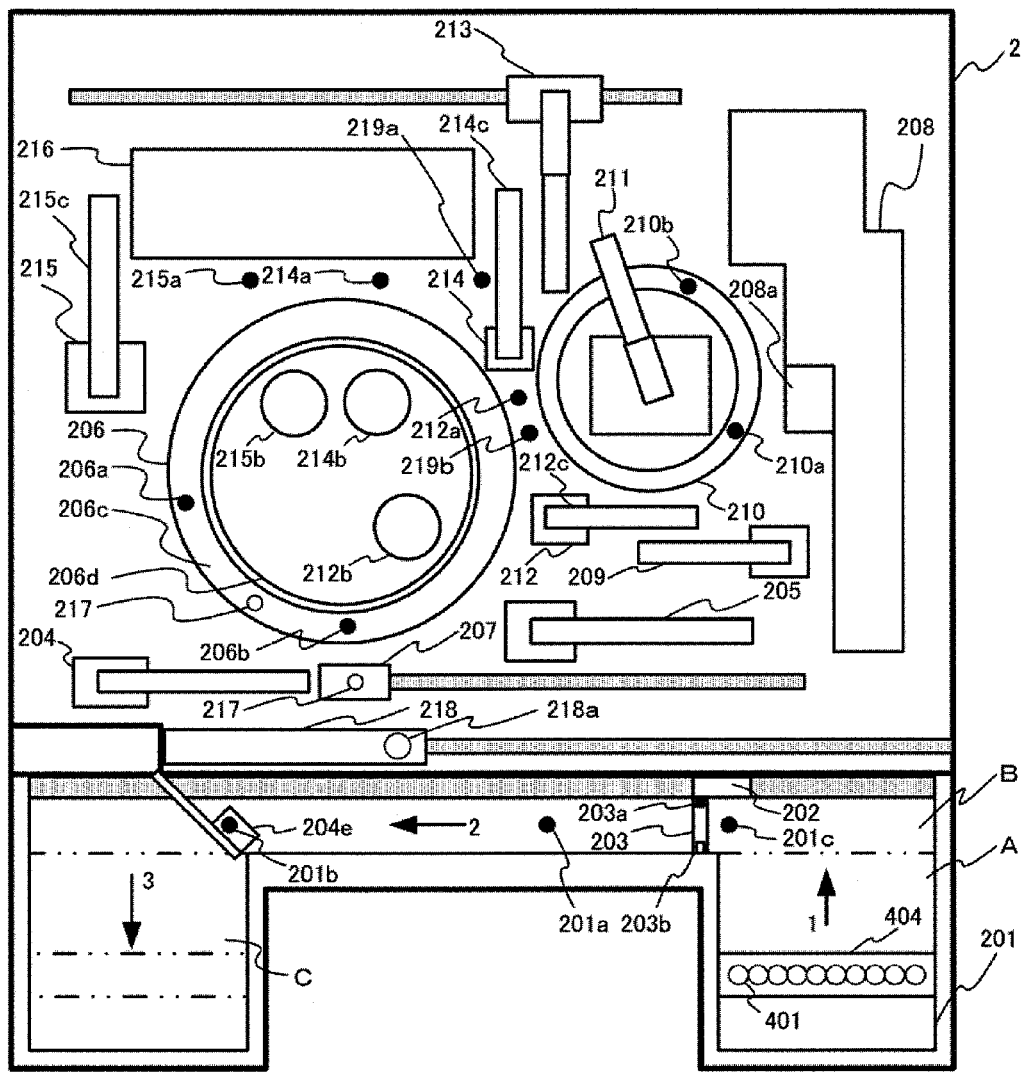
FIG. 2 is a schematic diagram showing a configuration of a measurement apparatus 2 according to the embodiment of the present invention.

FIG. 2 is a schematic diagram showing a configuration of the measurement apparatus 2. As shown in FIG. 2, the measurement apparatus 2 includes a transporting unit 201, a bar code reader unit 202, a sensor unit 203, a first dispensing unit 204, a second dispensing unit 205, a first table unit 206 having a reagent table 206d and a cuvette table 206c, a second table unit 207, a cuvette supplying unit 208, a first catcher unit 209, a heating table unit 210, a second catcher unit 211, a first reagent dispensing unit 212, a third catcher unit 213, a second reagent dispensing unit 214, a third reagent dispensing unit 215, a detection unit 216, and a buffer table unit 218 holding a diluent container 218a. The measurement apparatus 2 also includes a control unit 200 (see FIG. 3) which is not shown in FIG. 2.

Figure 3:
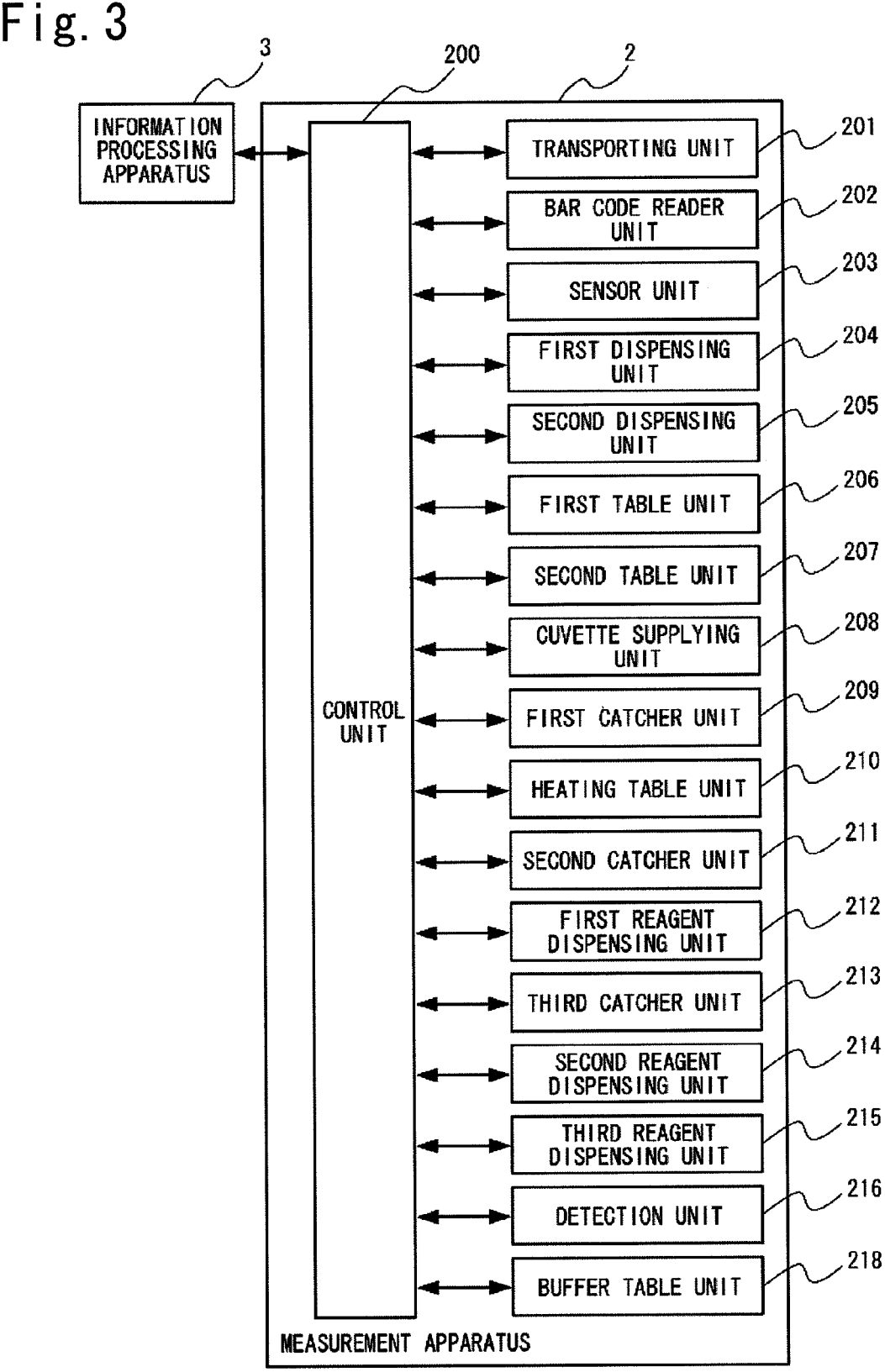
FIG. 3 is a block diagram showing a configuration of the measurement apparatus 2 according to the embodiment of the present invention.

FIG. 3 is a block diagram showing a configuration of the measurement apparatus 2. As shown in FIG. 3, the control unit 200 is interconnected with the transporting unit 201, the bar code reader unit 202, the sensor unit 203, the first dispensing unit 204, the second dispensing unit 205, the first table unit 206, the second table unit 207, the cuvette supplying unit 208, the first catcher unit 209, the heating table unit 210, the second catcher unit 211, the first reagent dispensing unit 212, the third catcher unit 213, the second reagent dispensing unit 214, the third reagent dispensing unit 215, the detection unit 216, and the buffer table unit 218. The control unit 200 is configured to be able to control the operation of each unit. The control unit 200 is communicably connected to the information processing apparatus 3.

Figure 4:
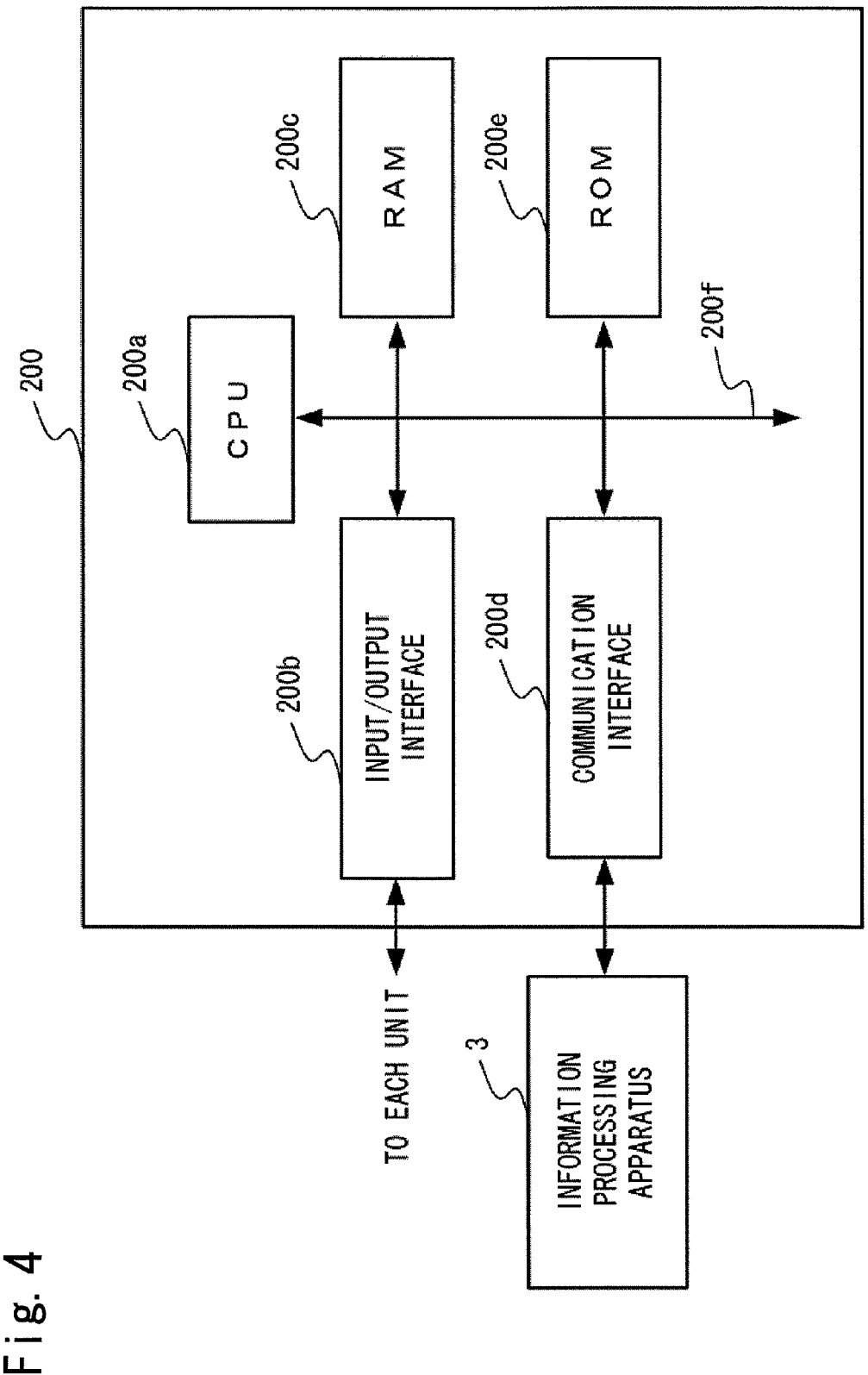
FIG. 4 is a block diagram showing a configuration of a control unit 200 according to the embodiment of the present invention.

FIG. 4 is a block diagram showing a configuration of the control unit 200. As shown in FIG. 4, the control unit 200 includes a CPU 200a, an input/output interface 200b, a RAM 200c, a communication interface 200d, and a ROM 200e. The CPU 200a, the input/output interface 200b, the RAM 200c, the communication interface 200d, and the ROM 200e are communicably connected to each other via a bus 200f.

The CPU 200a executes a computer program stored in the ROM 200e and a computer program loaded to the RAM 200c. The ROM 200e is structured as a mask ROM, PROM, EPROM, EEPROM or the like, and stores various computer programs to be executed by the CPU 200a and stores data to be used by these computer programs.

The RAM 200c is structured as an SRAM, DRAM or the like. The CPU 200a loads a computer program stored in the ROM 200e to the RAM 200c. The RAM 200c is used as a work area when the CPU 200a executes the computer program.

The input/output interface 200b outputs a command provided from the CPU 200a to each unit of the measurement apparatus 2. The input/output interface 200b receives information transmitted from each unit, and transmits the received information to the CPU 200a.

The communication interface 200d is an Ethernet (registered trademark) interface. By using a predetermined communication protocol (TCP/IP) and via the communication interface 200d, the measurement apparatus 2 is capable of transmitting/receiving data to/from the information processing apparatus 3 that is connected to the measurement apparatus 2 by a LAN cable.

Figure 5:
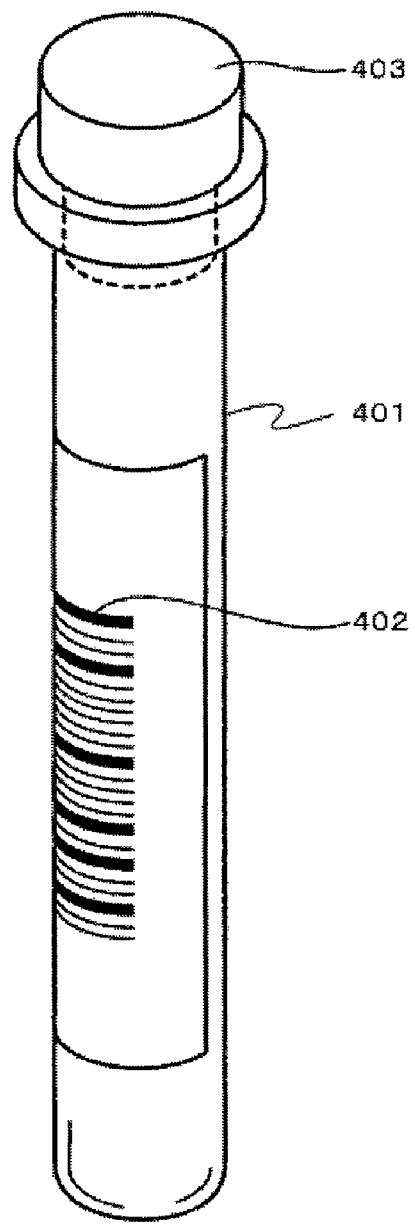
FIG. 5 is a perspective view showing a specimen container 401 according to the embodiment of the present invention.

FIG. 5 is a perspective view showing a structure of a specimen container 401. The specimen container 401 contains a specimen (in the present embodiment, a blood specimen) that is collected at a hospital or the like. As shown in FIG. 5, a bar code 402 containing identification information for identifying the specimen container 401, is attached to the specimen container 401. Among the specimen containers 401, some containers are each provided with a stopper (cap) 403 inserted into the opening thereof. Here, a specimen contained in the specimen container 401 whose opening is not sealed with the stopper 403, is measured in a first operation mode that is described later. Whereas, a specimen contained in the specimen container whose opening is sealed with the stopper 403, is measured in a second operation mode that is also described later.

Figure 6:
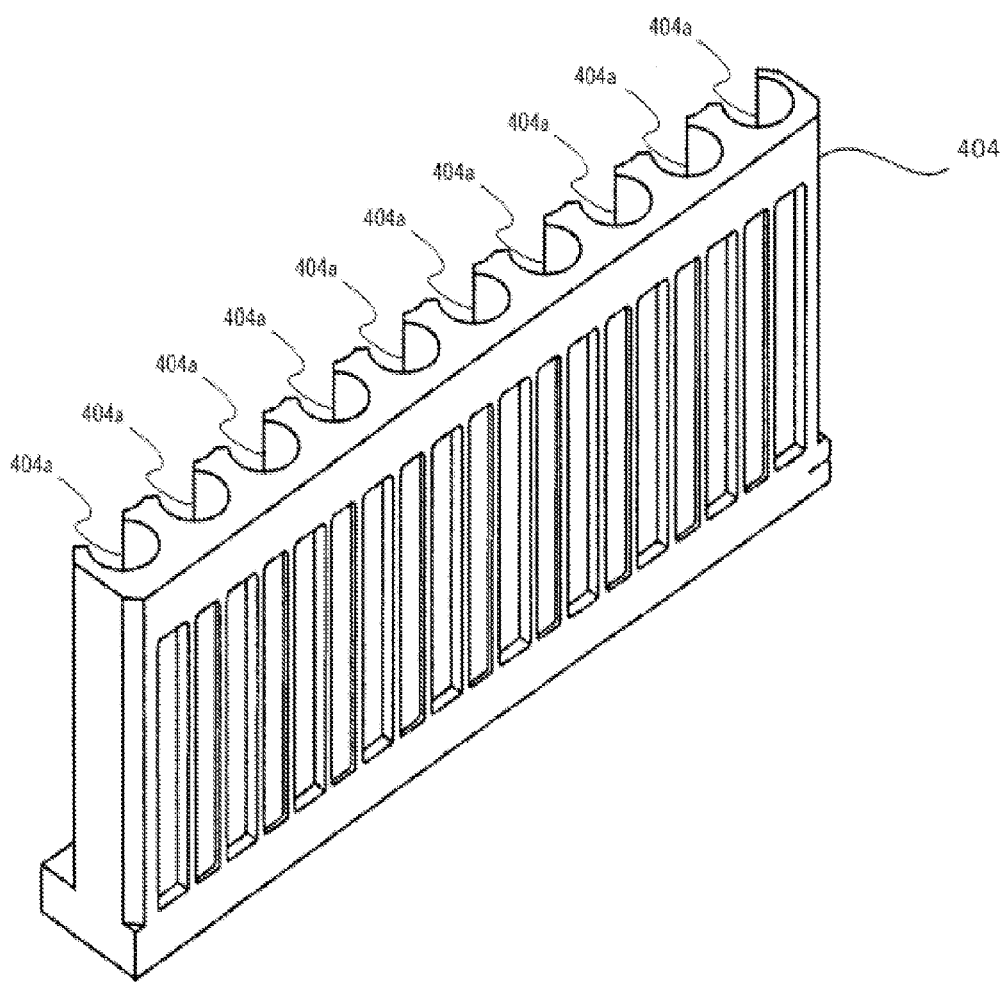
FIG. 6 is a perspective view showing a rack 404 according to the embodiment of the present invention.

FIG. 6 is a perspective view showing a structure of a rack 404. As shown in FIG. 6, the rack 404 is provided with ten holders 404a. These ten holders 404a each accommodate one specimen container 401. In the case where the size of the specimen containers 401 is smaller than that of the holders 404a, adaptors (not shown) may be attached to the holders 404a so that the specimen containers 401 can be prevented from tilting or falling.

Figure 7:
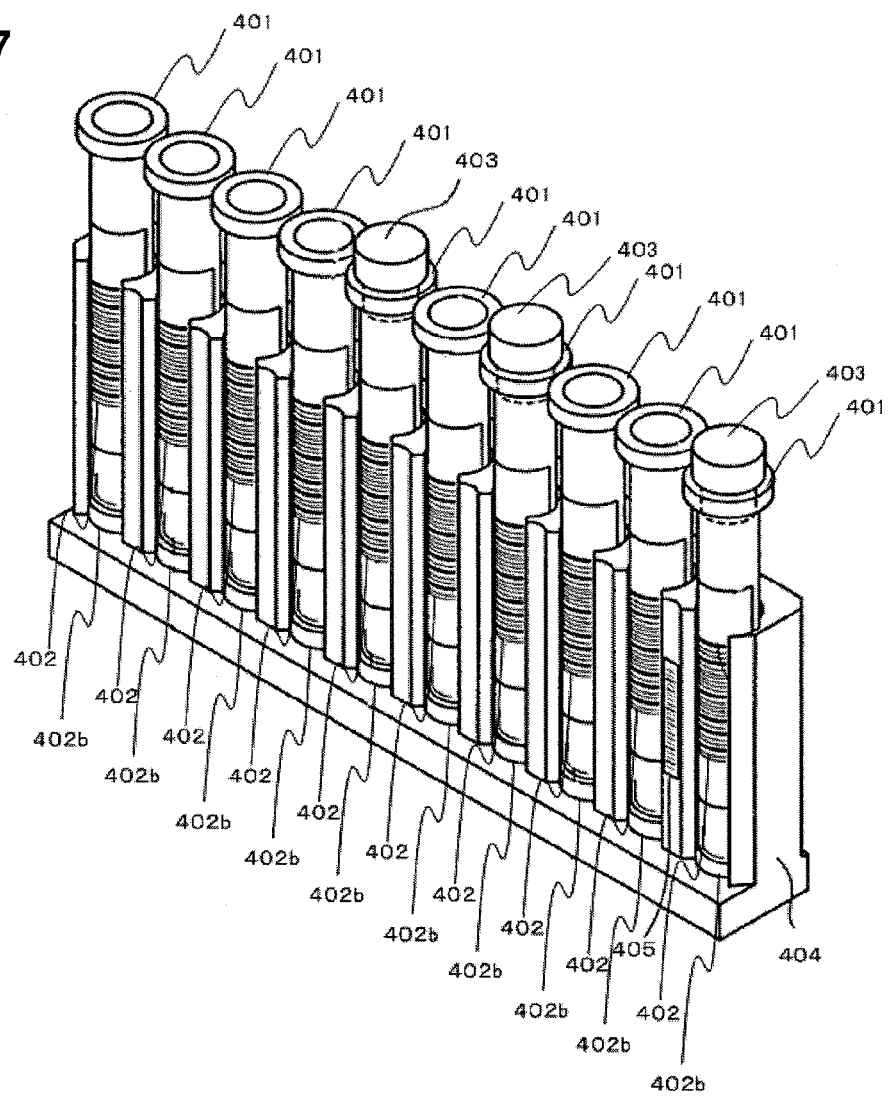
FIG. 7 is a perspective view showing that the rack 404 holds specimen containers 401 according to the embodiment of the present invention.

FIG. 7 is a perspective view showing that the rack 404 holds the specimen containers 401. As shown in FIG. 7, the rack 404 is provided with openings 402b so as to allow the bar codes 402 of the specimen containers 401 to be read by the bar code reader unit 202. Further, a bar code 405 containing identification information for identifying the rack 404, is attached to the rack 404.

Return to FIG. 2. The transporting unit 201 is capable of transporting the rack 404 holding the specimen containers 401. The transporting unit 201 includes: a rack set region A where the rack 404 holding the specimen containers 401 is to be set; a transport region B where the rack 404 previously set in the rack set region A is transported through; a rack storing region C for storing the rack 404 transported from the transport region B. The transporting unit 201 is capable of: transporting, in a direction indicated by an arrow 1, the rack 404 set in the rack set region A; transporting, in a direction indicated by an arrow 2, the rack 404 having entered the transport region B; and transporting, in a direction of an arrow 3, the rack 404 having entered the rack storing region C. The transport region B has an aspirating position 201a and an aspirating position 201b. The specimen contained in a specimen container 401 transported to the aspirating position 201b is aspirated by the first dispensing unit 204, and the specimen contained in a specimen container 401 transported to the aspirating position 201a is aspirated by the second dispensing unit 205.

The bar code reader unit 202 is capable of reading the bar codes 402 and the bar code 405 attached to the specimen containers 401 and the rack 404 within the transport region B. The bar code reader unit 202 is slidable on a slide rail that is provided in parallel to the transport region B. The bar code reader unit 202 is also capable of transmitting, to the control unit 200, the identification information contained in each bar code.

The sensor unit 203 is capable of obtaining information for the control unit 200 to determine presence or absence of the stopper 403 on a specimen container 401. The sensor unit 203 includes a light emitter 203a and a light receiver 203b, which are provided at upper right positions to the specimen aspirating position 201a in the transport region B so as to face each other, such that the stopper 403 or the opening of the specimen container 401 is to be positioned between the light emitter 203a and the light receiver 203b. When the stopper 403 is inserted into the specimen container 401, the stopper 403 blocks a light emitted from the light emitter 203a. As a result, the sensor unit 203 obtains information that the stopper 403 is inserted into the specimen container 401. When the stopper 403 is not inserted into the specimen container 401, the light emitted from the light emitter 203a is not blocked and illuminates the light receiver 203b. As a result, the sensor unit 203 obtains information that the stopper 403 is not inserted into the specimen container 401.

The first dispensing unit 204 is capable of aspirating the specimen from the specimen container 401 having been transported to the aspirating position 201b, and discharging the specimen into a cuvette 217 in a container position 206a on the cuvette table 206c.

Figure 8:
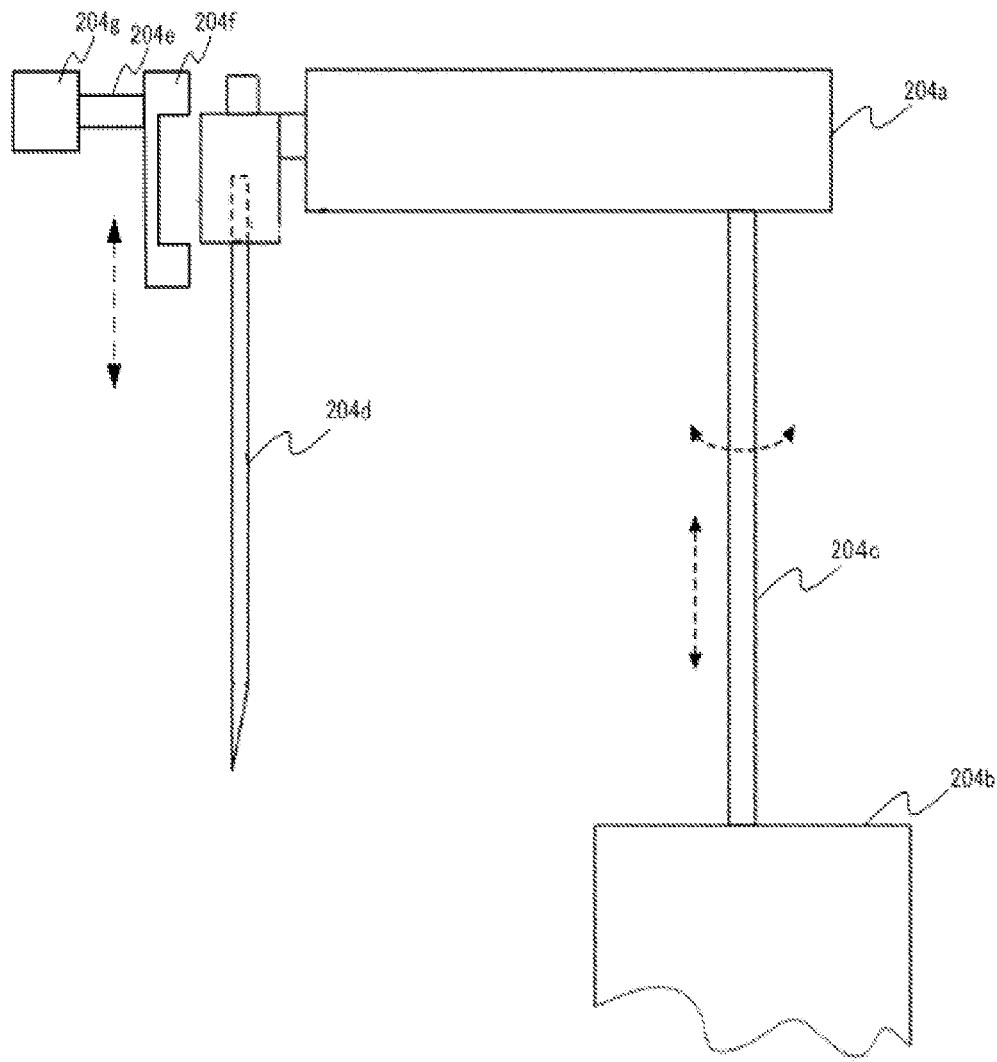
FIG. 8 is a schematic diagram showing a structure of a first dispensing unit 204 according to the embodiment of the present invention.

FIG. 8 is a schematic diagram showing a structure of the first dispensing unit 204. As shown in FIG. 8, the first dispensing unit 204 includes: an arm 204a; a driving section 204b for driving the arm 204a; a shaft 204c for supporting the arm 204a and transmitting a driving force of the driving section 204b to the arm 204a; a metal pipette 204d, fixed to the arm 204a, whose tip is diagonally cut to be sharp; and a pump (not shown) for aspirating and discharging the specimen. Here, the arm 204a of the first dispensing unit 204 is capable of rotating around the shaft 204c by the driving force of the driving section 204b, and also capable of moving in the up/down direction. Accordingly, by rotating the arm 204a, the pipette 204d of the first dispensing unit 204 can be disposed above the aspirating position 201b or above the container position 206a.

An assisting mechanism 204e is provided above the aspirating position 201b. The assisting mechanism 204e assists the first dispensing unit 204 in dispensing the specimen. The assisting mechanism 204e has an engagement member 204f engageable with the arm 204a, and has a driving section 204g that produces, in the up/down direction, a greater driving force than that of the driving section 204b. Here, the engagement member 204f is movable in the up/down direction by the driving force of the driving section 204g. When the stopper 403 is inserted into the specimen container 401, the first dispensing unit 204 causes the engagement member 204f of the assisting mechanism 204e to be engaged with the arm 204a, whereby a strong downward driving force of the driving section 204g is transmitted to the arm 204a and to the pipette 204d. This allows the first dispensing unit 204 to penetrate through the stopper 403 and aspirate the specimen contained in the specimen container 401.

Return to FIG. 2. The second dispensing unit 205 is capable of aspirating the specimen from the specimen container 401 having been transported by the transporting unit 201 to the aspirating position 201a, and discharging the specimen into a cuvette 217 held by the second table unit 207. The second dispensing unit 205 is also capable of aspirating, from the cuvette 217 which is in a container position 206b and into which the first dispensing unit 204 has dispensed the specimen, a predetermined portion of the specimen depending on a measurement item, and discharging the predetermined portion of the specimen into the cuvette 217 on the second table unit 207. Here, the specimen remains in the cuvette 217 in the container position 206b, in a particular amount that allows the measurement of the specimen to be performed again.

The second dispensing unit 205 is further capable of aspirating a diluent from the diluent container 218a held by the buffer table 218, aspirating a predetermined amount of air, aspirating the specimen from the cuvette 217 in the container position 206b or from the specimen container 401 in the aspirating position 201a, and discharging them into the cuvette 217 on the second table unit 207, thereby diluting the specimen.

Figure 9:
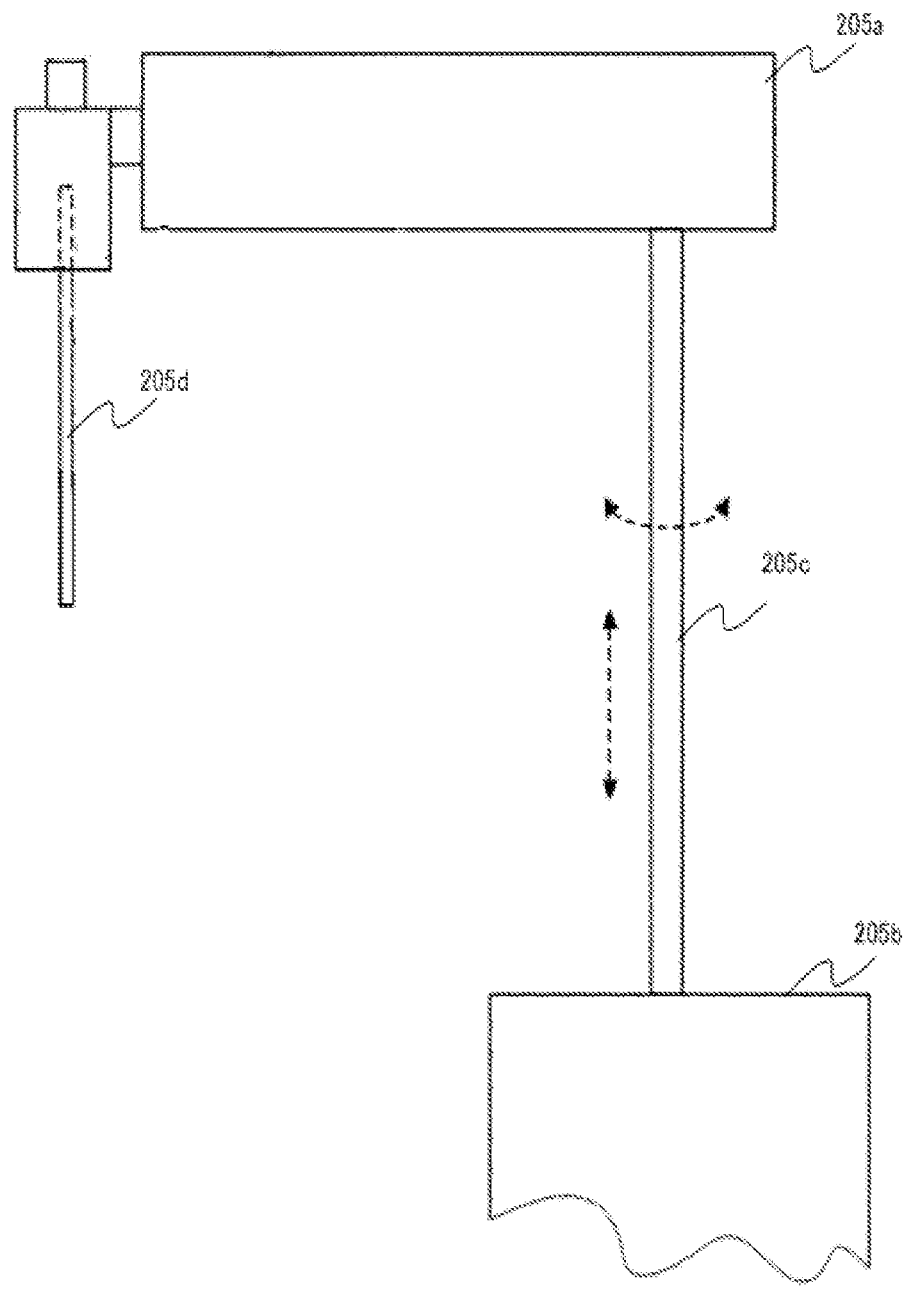
FIG. 9 is a schematic diagram showing a structure of a second dispensing unit 205 according to the embodiment of the present invention.

FIG. 9 is a schematic diagram showing a structure of the second dispensing unit 205. As shown in FIG. 9, the second dispensing unit 205 includes: an arm 205a; a driving section 205b for driving the arm 205a; a shaft 205c for supporting the arm 205a and transmitting a driving force of the driving section 205b; a pipette 205d fixed to the arm 205a; and a pump (not shown) for aspirating and discharging the specimen. Here, the arm 205a is capable of rotating around the shaft 205c by the driving force of the driving section 205b, and also capable of moving in the up/down direction. Accordingly, the pipette 205d of the second dispensing unit 205 can be disposed above the aspirating position 201a or above the cuvette 217 on the second table unit 207. Further, the pipette 205d and the pump of the second dispensing unit 205 are designed and configured to be able to aspirate the specimen by a less amount than the amount of specimen which the pipette 204d and the pump of the first dispensing unit 204 can aspirate.

Figure 15:
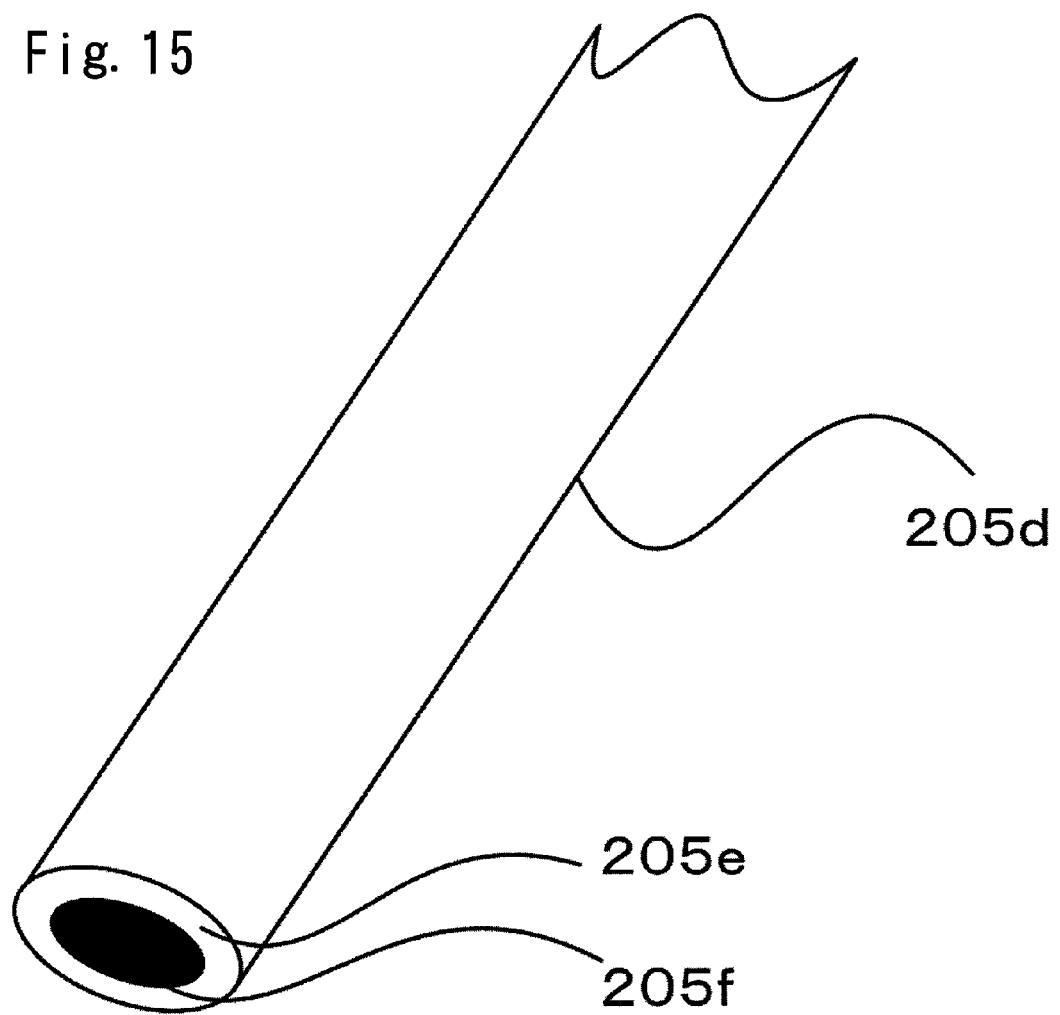
FIG. 15 is a perspective view showing a structure of a pipette 205d according to the embodiment of the present invention.

FIG. 15 is a perspective view showing a structure of the pipette 205d. As shown in FIG. 15, a horizontally flat surface 205e is formed at the tip of the pipette 205d. An opening 205f is formed at the flat surface 205e. When the pump operates to aspirate the specimen, the specimen is aspirated into the pipette 205d through the opening 205f. Owing to this structure of the pipette 205d, the second dispensing unit 205 is able to aspirate the specimen that is near the bottom of the specimen container.

Return to FIG. 2. The reagent table 206d of the first table unit 206 is a round table capable of holding: a first reagent container 212b that contains a first reagent; a second reagent container 214b that contains a second reagent; and a third reagent container 215b that contains a third reagent. The reagent table 206d is capable of rotating in both the clockwise direction and the counterclockwise direction. Further, a cooling device (not shown) including a peltiert device is provided in a position vertically downward from the reagent table 206d for the purpose of keeping cool the reagents contained in the reagent containers.

The cuvette table 206c of the first table unit 206 is provided outside the reagent table 206d. The cuvette table 206c is an annular table capable of holding cuvettes 217 via insertion holes (not shown) provided therein.

Here, by rotating in the clockwise direction or in the counter clockwise direction, the cuvette table 206c can move a cuvette 217 to the container position 206a or to the container position 206b.

The second table unit 207 is capable of holding a cuvette 217 via an insertion hole (not shown) provided therein, and movable on a slide rail that is provided in parallel to the slide rail of the bar code reader unit 202. The second table unit 207 stands by, holding a vacant cuvette 217 at the left end of the slide rail. The second table unit 207 is also capable of moving to the right end of the slide rail, while holding the cuvette 217 into which the specimen has been dispensed by the second dispensing unit 205.

The buffer table unit 218 is capable of holding the diluent container 218a that contains a diluent to be used for diluting the specimen, and capable of moving on a slide rail that is provided in parallel to the slide rail of the bar code reader unit 202.

The cuvette supplying unit 208 is capable of sequentially supplying, to a cuvette storing section 208a, a plurality of cuvettes 217 which have been fed into the cuvette supplying unit 208 at random by a user. Here, the cuvettes 217 having been supplied to the cuvette storing section 208a are each transferred by the second catcher unit 211 to the cuvette table 206c or by the first catcher unit 209 to the second table unit 207.

The first catcher unit 209 is capable of transferring, to a container position 210a of the heating table unit 210, the cuvette 217 that is held by the second table unit 207 having moved to the right end of the slide rail thereof (slide rail 207a). Also, the first catcher unit 209 is capable of, in the case where the second table unit 207 having moved to the right end of the slide rail 207a is not holding a cuvette 217, transferring a cuvette 217 stored in the cuvette storing section 208a to the second table unit 207.

The heating table unit 210 is capable of holding the cuvette 217 and heating, for a predetermined period, the specimen contained in the cuvette 217. The heating table unit 210 is an annular table provided with a plurality of insertion holes (not shown) for holding cuvettes 217. The heating table unit is rotatable in the clockwise direction and in the counter clockwise direction. The heating table unit 210 is capable of moving the cuvette 217 in the container position 210a to a container position for heating (not shown) or to a container position 210b. The heating table unit 210 is also provided with a heater (not shown). Therefore, the heating table unit 210 is capable of heating the specimen contained in the cuvette 217.

The second catcher unit 211 is provided at a position surrounded by the annular heating table unit 210, and capable of transferring a cuvette 217 by rotating. The second catcher unit 211 is capable of transferring the cuvette 217 from the heating table unit 210 to a position above a first reagent dispensing position 212a, and holding the cuvette 217 at the position. Further, the second catcher unit 211 is capable of transferring the cuvette 217 into which the first reagent has been dispensed, from the position above the first reagent dispensing position 212a to the heating table unit 210. Still further, the second catcher unit 211 is capable of transferring a cuvette 217 stored in the cuvette storing section 208a to the cuvette table 206c.

The first reagent dispensing unit 212 is capable of dispensing the first reagent contained in the first reagent container 212b, into the cuvette 217 that is held by the second catcher unit 211 at the position above the first reagent dispensing position 212a.

The third catcher unit 213 is movable on a slide rail that is provided in parallel to the slide rail of the second table unit 207. The third catcher unit 213 is capable of transferring the cuvette 217 in the container position 210b of the heating table unit 210 to a position above a second reagent dispensing position 214a or to a position above a third reagent dispensing position 215a, and holding the cuvette 217 at the position. Further, the third catcher unit 213 is capable of transferring the cuvette 217 to the detection unit 216 from the position above the second reagent dispensing position 214a or from the position above the third reagent dispensing position 215a.

The second reagent dispensing unit 214 is capable of dispensing the second reagent contained in the second reagent container 214b into the cuvette 217 that is held, by the third catcher unit 213, in the position above the second reagent dispensing position 214a.

The third reagent dispensing unit 215 is capable of dispensing the third reagent contained in the third reagent container 215b into the cuvette 217 that is held, by the third catcher unit 213, in the position above the third reagent dispensing position 215a.

The detection unit 216 is capable of optically measuring the specimen contained in the cuvette 217 that is transferred to the detection unit 216 by the third catcher unit 213, thereby detecting optical information about the specimen. The detection unit 216 is provided with a plurality of insertion holes (not shown) for holding cuvettes 217. When emitting light to each of the specimens in the cuvettes 217 inserted into the insertion holes, the detection unit 216 is capable of detecting transmitted light and scattered light, and outputting electrical signals that correspond to the detected transmitted light and scattered light, respectively. Also, the detection unit 216 is capable of heating the specimens contained in the cuvettes 217 inserted into the insertion holes.

Note that, the measurement apparatus 2 is provided with cuvette disposal holes 219a and 219b for disposing of cuvettes 217. Among cuvettes 217 containing specimens on which the measurement has been performed, cuvettes held by the detection unit 216 are fed by the third catcher unit 213 into the cuvette disposal hole 219a and cuvettes held by the cuvette table 206c are fed by the second catcher unit 211 into the cuvette disposal hole 219b, respectively. These cuvettes 217 fed into the cuvette disposal holes 219a and 219b are dropped to a cuvette disposal section (not shown) that is provided below the measurement apparatus 2.

Return to FIG. 1. The information processing apparatus 3 is structured as a computer. The information processing apparatus 3 includes a control section 301, a display section 302, and an input device 303. The information processing apparatus 3 transmits a measurement start signal to the measurement apparatus 2. Based on identification information received from the measurement apparatus 2, the information processing apparatus 3 inquires of a host computer about a measurement order that contains information such as a measurement item, an operation mode and the like. The information processing apparatus 3 transmits, to the measurement apparatus 2, information such as the measurement item, operation mode and the like which are received from the host computer. The information processing apparatus 3 also analyzes a result of measuring a specimen, which result is received from the measurement apparatus 2.

Figure 10:
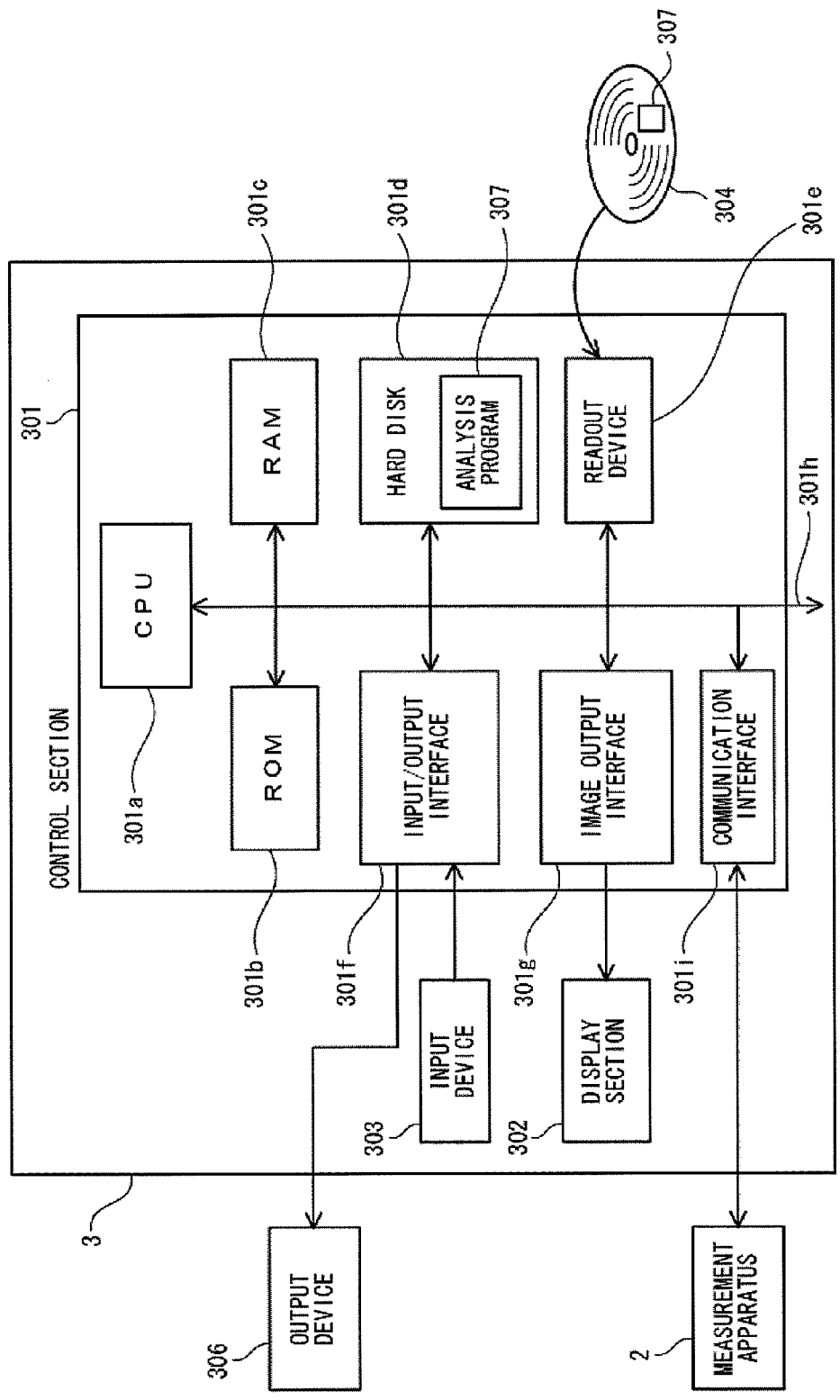
FIG. 10 is a block diagram showing a configuration of an information processing apparatus 3 according to the embodiment of the present invention.

FIG. 10 is a block diagram showing a configuration of the information processing apparatus 3. Here, as shown in FIG. 10, the control section 301 includes a CPU 301a, a ROM 301b, a RAM 301c, a hard disk 301d, a readout device 301e, an input/output interface 301f, an image output interface 301g, and a communication interface 301i. The CPU 301a, ROM 301b, RAM 301c, hard disk 301d, readout device 301e, input/output interface 301f, image output interface 301g, and the communication interface 301i are connected to each other via a bus 301h.

The CPU 301a is provided for the purpose of executing a computer program stored in the ROM 301b and a computer program loaded into the RAM 301c. The ROM 301b is structured as a mask ROM, PROM, EPROM, EEPROM or the like. The ROM 301b stores, for example, a computer program to be executed by the CPU 301a, and stores data used by the computer program.

The RAM 301c is structured as an SRAM, DRAM or the like. The RAM 301c is used for reading computer programs stored in the ROM 301b and the hard disk 301d. The RAM 301c is used as a work area of the CPU 301a at the time of execution of these computer programs.

Installed in the hard disk 301d are: various computer programs to be executed by the CPU 301a, such as an operating system and application programs; and data to be used for executing these computer programs.

The readout device 301e is structured as a flexible disc drive, CD-ROM drive, DVD-ROM drive or the like. The readout device 301e is capable of reading a computer program or data, which is stored in a portable storage medium 304. The portable storage medium 304 stores therein an analysis program 307. The CPU 301a is capable of controlling the readout device 301e so as to read the analysis program 307 from the portable storage medium 304, and storing the read analysis program 307 in the hard disk 301d.

Also, an operating system that provides a graphical user interface environment, for example, Windows (registered trademark) manufactured and sold by Microsoft Corporation, is installed in the hard disk 301d.

For example, the input/output interface 301f is configured as: a serial interface such as USB, IEEE1394 or RS-232C; a parallel interface such as SCSI, IDE or IEEE1284; or an analogue interface including a D/A converter, A/D converter and the like. The input device 303 including a keyboard and a mouse is connected to the input/output interface 301f. An operator can input data to the information processing apparatus 3, by using the input device 303. The output device 306 including a printer or the like is connected to the input/output interface 301f.

The communication interface 301i is an Ethernet (registered trademark) interface. The information processing apparatus 3 is capable of transmitting/receiving data to/from the measurement apparatus 2 connected thereto by a LAN cable, by means of the communication interface 301i and a predetermined communication protocol (TCP/IP).

Note that, the analysis program 307 can be provided to the information processing apparatus 3 not only via the portable storage medium 304, but also from an external device via a telecommunication line, which external device is connected to the communication interface 301i by the telecommunication line (regardless of wired or wireless). For example, the analysis program 307 is stored in a hard disk of a server computer on the Internet. The CPU 301a can access the server computer, and download the analysis program 307 from the server computer and store the analysis program 307 in the hard disk 301d.

The image output interface 301g is connected to the display section 302 that is structured with an LCD, CRT or the like. The image output interface 301 g outputs, to the display section 302, video signals supplied from the CPU 301a. The display section 302 displays an image (a screen), based on the video signals inputted from the image output interface 301g.

Figure 11:
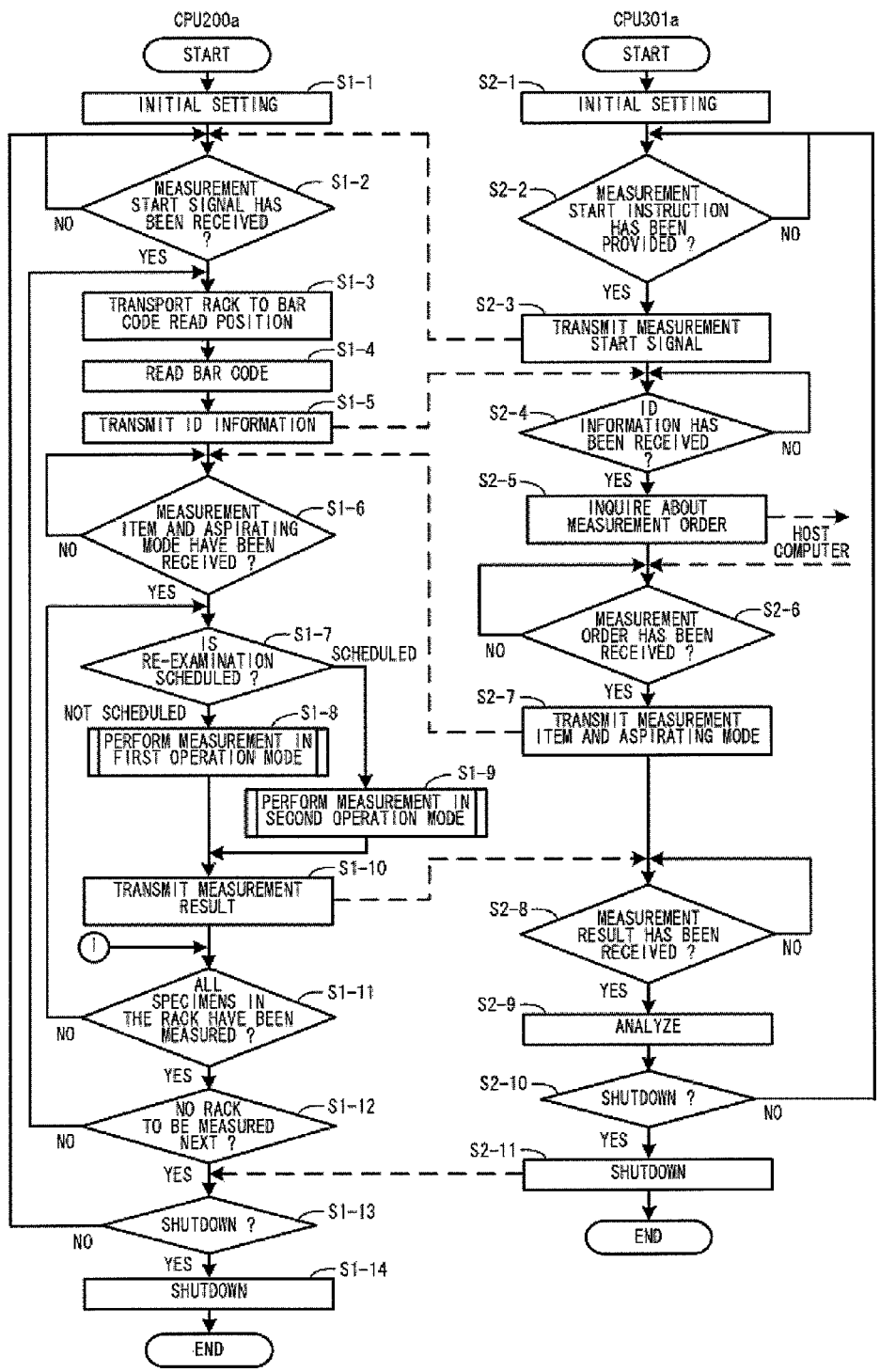
FIG. 11 is a flowchart showing a specimen analyzing process performed by the specimen analyzing apparatus 1 according to the embodiment of the present invention.

FIG. 11 is a flowchart showing a specimen analyzing process performed by the specimen analyzing apparatus 1. Hereinafter, operations of the measurement apparatus 2 and the information processing apparatus 3 will be described with reference to the flowchart illustrated in FIG. 11.

First, at step S1-1, the CPU 200a performs an initial setting process. In the initial setting process, the respective units are arranged in initial positions. The CPU 200a controls the cuvette supplying unit 208 in order to supply cuvettes 217 to the cuvette storing section 208a. The CPU 200a also controls the first catcher unit 209 and the second catcher unit 211 in order to transfer the cuvettes 217 stored in the cuvette storing section 208a to the second table unit 207 and the cuvette table 206c.

When the initial setting process ends, the CPU 200a waits, at step S1-2, for reception of a measurement start signal transmitted from the CPU 301a.

Meanwhile, at step S2-1, the CPU 301a performs an initial setting process. In the initial setting process, software stored in the hard disk 301d and the like is initialized.

When the initial setting process ends, the CPU 301a waits, at step S2-2, for reception of an input from an operator, the input indicating a measurement start instruction. When the input of the measurement start instruction is received from the operator (YES at step S2-2), the CPU 301a transmits, at step S2-3, a measurement start signal to the measurement apparatus 2.

Upon receiving the measurement start signal (YES at step S1-2), the CPU 200a controls the transporting unit 201 at step S1-3 so as to transport the rack 404 disposed in the rack set region A to a bar code read position 201c.

Next, at step S1-4, the CPU 200a controls the bar code reader unit 202 so as to read the bar code 405 attached to the rack 404 having been transported to the bar code read position 201c, and to read the bar codes 402 attached to the specimen containers 401 held by the rack 404.

Next, at step S1-5, the CPU 200a transmits, to the CPU 301a, identification information contained in the bar codes 402 and the bar code 405 which have been read by the bar code reader unit 202.

Hereinafter, the identification information contained in the bar codes 402 and the bar code 405 will be described. The bar codes 402 contain specimen identification information for identifying the specimens contained in the specimen containers 401. The specimen identification information is set in the form of sequential numbers such as C001, C002, C003, and so on. The bar code 405 contains rack identification information for identifying the rack 404. The rack identification information is also set in the form of sequential numbers such as R001, R002, R003, and so on. Further, the CPU 200a transmits, to the information processing apparatus 3, container positions that indicate which holders 404a of the rack 404 are holding the specimen containers 401. The container positions are represented by sequential integers such as 1, 2, ..., 9, 10 and so on. These numbers are assigned to the container positions, respectively.

Meanwhile, at step S2-4, the CPU 301 a waits for reception of the identification information from the CPU 200a. Upon receiving the identification information (YES at step S2-4), the CPU 301a inquires, at step S2-5, of the host computer about measurement items and re-examination schedules which correspond to the identification information and the container positions transmitted from the CPU 200a. Such information is contained in a measurement order registered in the host computer. Here, the CPU 301 a transmits, to the host computer, either a combination of the identification information about the rack 404 and the container positions, or the identification information about the specimen containers 401.

FIG. 14 is a schematic diagram showing an example of the measurement order. The operator of the specimen analyzing apparatus 1 registers the measurement order with the host computer before the specimen analyzing apparatus 1 analyzes the specimens. As shown in FIG. 14, the registered measurement order is associated with rack identification information, container positions, specimen identification information, measurement items, and re-examination schedules. For example, each measurement item is represented by "Fbg" if fibrinogen is to be measured for the corresponding specimen, or by "PT" if a prothrombin time is to be measured for the corresponding specimen. Also, each re-examination schedule is set to "SCHEDULED" if the specimen contained in the corresponding specimen container 401 requires re-examination to be performed thereupon, or set to "NOT SCHEDULED" if the specimen contained in the corresponding specimen container 401 does not require re-examination to be performed thereupon.

Upon receiving the combination of the identification information about the rack 404 and the container positions, or receiving the identification information about the specimen containers 401, the host computer transmits, to the CPU 301a, corresponding measurement items and re-examination schedules. For example, assume that the CPU 301a transmits information for identifying a specimen to the host computer at step S2-5, the information indicating that "the identification information about the rack is R001 and the container position is 1". In this case, the host computer refers to the measurement order as shown in FIG. 14, and then transmits, to the CPU 301a, information indicating that "the measurement item is Fbg and the re-examination schedule is NOT SCHEDULED".

After inquiring of the host computer about the measurement order, the CPU 301a waits, at step S2-6, for reception of the measurement items and the re-examination schedules transmitted from the host computer.

Upon receiving from the host computer the measurement items and the re-examination schedules for the respective specimens (YES at step S2-6), the CPU 301a transmits the measurement items and the re-examination schedules to the CPU 200a at step S2-7.

Meanwhile, the CPU 200a waits, at step S1-6, for reception of the measurement items and the re-examination schedules from the CPU 301a. Upon receiving the measurement items and the re-examination schedules transmitted from the CPU 301a (YES at step S1-6), the CPU 200a determines at step S1-7 whether to measure the specimen contained in the specimen container 401 that is currently a measurement target, in the first operation mode or in the second operation mode, based on whether the re-examination schedule of the specimen is "SCHEDULED" or "NOT SCHEDULED".

When it is determined at step S1-7 that the re-examination schedule is "NOT SCHEDULED" (NOT SCHEDULED at step S1-7), the CPU 200a performs the measurement in the first operation mode at step S1-8. Whereas, when it is determined at step S1-7 that the re-examination schedule is "SCHEDULED" (SCHEDULED at step S1-7), the CPU 200a performs the measurement in the second operation mode at step S1-9. Here, the measurement in the first operation mode is a measurement process that includes a process of dispensing, from the specimen container 401, the specimen by an amount that allows the measurement to be performed once for one measurement item. Also, the measurement in the second operation mode is a measurement process that includes a process of dispensing, from the specimen container 401, the specimen by an amount that allows the measurement to be performed a plurality of times for one measurement item. Note that, the measurement processes in the first operation mode and in the second operation mode will be described later in detail.

When the measurement process in the first operation mode or in the second operation mode ends, the CPU 200a transmits measurement results of the specimen to the CPU 301a at step S1-10.

Next, at step S1-11, the CPU 200a determines whether or not the measurement of the specimens contained in all the specimen containers 401 held by the rack 404 has ended. When it is determined that the measurement of all the specimens held by the rack 404 has not ended yet (NO at step S1-11), the CPU 200a performs the process at step S1-7.

When it is determined that the measurement of the specimens contained in all the specimen containers 401 held by the rack 404 has ended (YES at step S1-11), the CPU 200a controls the third catcher unit 213 and the second catcher unit 211 at step S1-12 so as to drop cuvettes 217 held by the detection unit 216 and cuvettes 217 held by the cuvette table 206c into the cuvette disposal hole 219a and the cuvette disposal hole 219b, respectively. These cuvettes 217 contain specimens on which the measurement has been completed.

Next, the CPU 200a determines at step S1-12 whether or not a rack 404 to be measured is present in the rack set region A. If a rack 404 to be measured is present in the rack set region A (NO at step S1-12), the CPU 200a performs the process at step S1-3. At the same time, the CPU 200a controls the transporting unit 201 so as to transport the rack 404 in the transport region B to the rack storing region C.

Meanwhile, the CPU 301a waits, at step S2-8, for reception of the measurement results transmitted from the CPU 200a. Upon receiving the measurement results (YES at step S2-8), the CPU 301a performs, at step S2-9, a process of analyzing the measurement results. Here, based on the optical information about the scattered light, the transmitted light and the like measured by the measurement apparatus 2, the CPU 301a calculates an analysis result such as a prothrombin time (PT), fibrinogen (Fbg) or the like of the specimen, and causes the display section 302 to display the analysis result.

Next, the CPU 301a determines at step S2-10 whether or not the operator has provided a shutdown instruction. When it is determined that the shutdown instruction has been provided (YES at step S2-10), the CPU 301a transmits, at step S2-11, a shutdown instruction to the measurement apparatus 2 and performs a shutdown process. When it is determined that the shutdown instruction has not been provided (NO at step S2-11), the CPU 301a performs the process at step S2-2.

When it is determined that a rack 404 to be measured is not present in the rack set region A (YES at step S1-12), the CPU 200a determines at step S1-13 whether or not the shutdown instruction has been received from the CPU 301a. When it is determined that the shutdown instruction has been received (YES at step S1-13), the CPU 200a performs a shutdown process at step S1-14. When it is determined that the shutdown instruction has not been received (NO at step S1-13), the CPU 200a performs the process at step S1-2.

Figure 12:
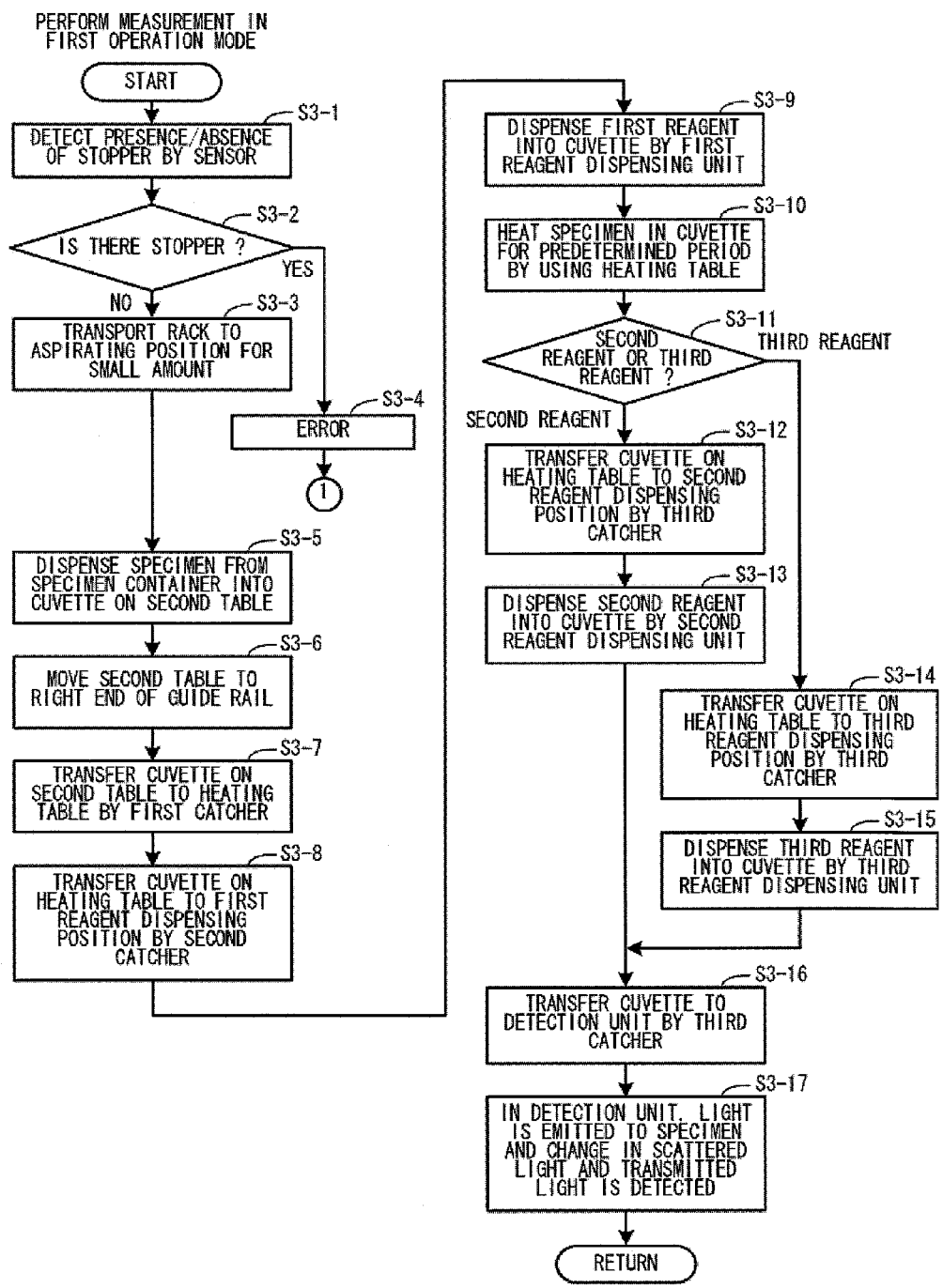
FIG. 12 is a flowchart showing a specimen measuring operation that is performed, in a first operation mode, by the measurement apparatus 2 according to the embodiment of the present invention.

FIG. 12 is a flowchart showing a specimen measuring operation performed in the first operation mode. Hereinafter, the specimen measuring operation in the first operation mode will be described with reference to FIG. 12.

The CPU 200a confirms, at step S3-1 by means of the sensor unit 203, whether or not the stopper 403 is inserted into the specimen container 401, held by the rack 404, in the bar code read position 201c. Next, at step S3-2, the CPU 200a determines, based on a result of the confirmation at step S3-1, whether or not the stopper 403 is inserted into the specimen container 401. When it is determined that the stopper 403 is inserted into the specimen container 401 (YES at step S3-2), the CPU 200a performs error handling at step S3-4. Thereafter, the process at step S1-11 is performed.

When it is determined that the stopper 403 is not inserted into the specimen container 401 (NO at step S3-2), the CPU 200a controls the transporting unit 201 at step S3-3 so as to transport the rack 404 in the bar code read position 201c to the aspirating position 201a.

Next, at step S3-5, the CPU 200a controls the second dispensing unit 205 so as to dispense the specimen in the specimen container 401 in the aspirating position 201a, into a cuvette 217 held by the second table unit 207. First, the arm 205a rotates, whereby the pipette 205d is disposed above the aspirating position 201a. Next, a downward driving force of the driving section 205b causes the arm 205a and the pipette 205d to descend. Next, the specimen in the specimen container 401 is aspirated by the pipette 205d and the pump. Next, an upward driving force of the driving section 205b causes the arm 205a and the pipette 205d to ascend. Subsequently, the arm 205a rotates, whereby the pipette 205d is disposed above the cuvette 217. Then, the specimen is discharged into the cuvette 217 by the pipette 205d and the pump.

Next, at step S3-6, the CPU 200a controls the second table unit 207 such that the second table unit 207 moves to the right end of the slide rail.

Subsequently, at step S3-7, the CPU 200a controls the first catcher unit 209 in order to transfer the cuvette 217 held by the second table unit 207 to the heating table unit 210. Here, the CPU 200a controls the first catcher unit 209 so as to transfer a new cuvette 217 to the second table unit 207. Further, the CPU 200a controls the second table unit 207 holding the new cuvette 217 such that the second table unit 207 moves to the left end of the slide rail.

Next, at step S3-8, the CPU 200a controls the second catcher unit 211 so as to transfer the cuvette 217 from the heating table unit 210 to a position above the first reagent dispensing position 212a and hold the cuvette 217 at the position. Then, the CPU 200a controls the first reagent dispensing unit 212 at step S3-9 in order to dispense the first reagent into the cuvette 217 held above the first reagent dispensing position 212a.

Next, at step S3-10, the CPU 200a controls the second catcher unit 211 in order to transfer the cuvette 217 from the position above the first reagent dispensing position 212a to the heating table unit 210. Also, the CPU 200a controls the heating table unit 210 so as to heat, for a predetermined period, the specimen in the cuvette 217 having been transferred to the heating table unit 210.

When the specimen contained in the cuvette 217 has been heated for the predetermined period, the CPU 200a determines, at step S3-11, whether to dispense the second reagent into the cuvette 217 or to dispense the third reagent into the cuvette 217.

When it is determined at step S3-11 to dispense the second reagent ("SECOND REAGENT" at step S3-11), the CPU 200a controls the third catcher unit 213 at step S3-12 in order to transfer the cuvette 217 from the container position 210b of the heating table unit 210 to a position above the second reagent dispensing position 214a and hold the cuvette 217 at the position. Next, at step S3-13, the CPU 200a controls the second reagent dispensing unit 214 so as to dispense the second reagent into the cuvette 217 held above the second reagent dispensing position 214a.

When it is determined at step S3-11 to dispense the third reagent ("THIRD REAGENT" at step S3-11), the CPU 200a controls the third catcher unit 213 at step S3-14 so as to transfer the cuvette 217 from the container position 210b of the heating table unit 210 to a position above the third reagent dispensing position 215a and hold the cuvette 217 at the position. Next, at step S3-15, the CPU 200a controls the third reagent dispensing unit 215 in order to dispense the third reagent into the cuvette 217 held above the third reagent dispensing position 215a.

Next, at step S3-16, the CPU 200a controls the third catcher unit 213 so as to transfer the cuvette 217, into which the second reagent has been dispensed, from the position above the second reagent dispensing position 214a to an insertion hole of the detection unit 216, or to transfer the cuvette 217, into which the third reagent has been dispensed, from the position above the third reagent dispensing position 215a to an insertion hole of the detection unit 216.

Next, at step S3-17, the CPU 200a controls the detection unit 216 in order to emit light to the specimen in the cuvette 217 inserted into the insertion hole of the detection unit 216. At this point, electrical signals corresponding to detected transmitted light and scattered light, respectively, are outputted from the detection unit 216. Thereafter, the CPU 200a performs the process at step S1-10.

Figure 13:
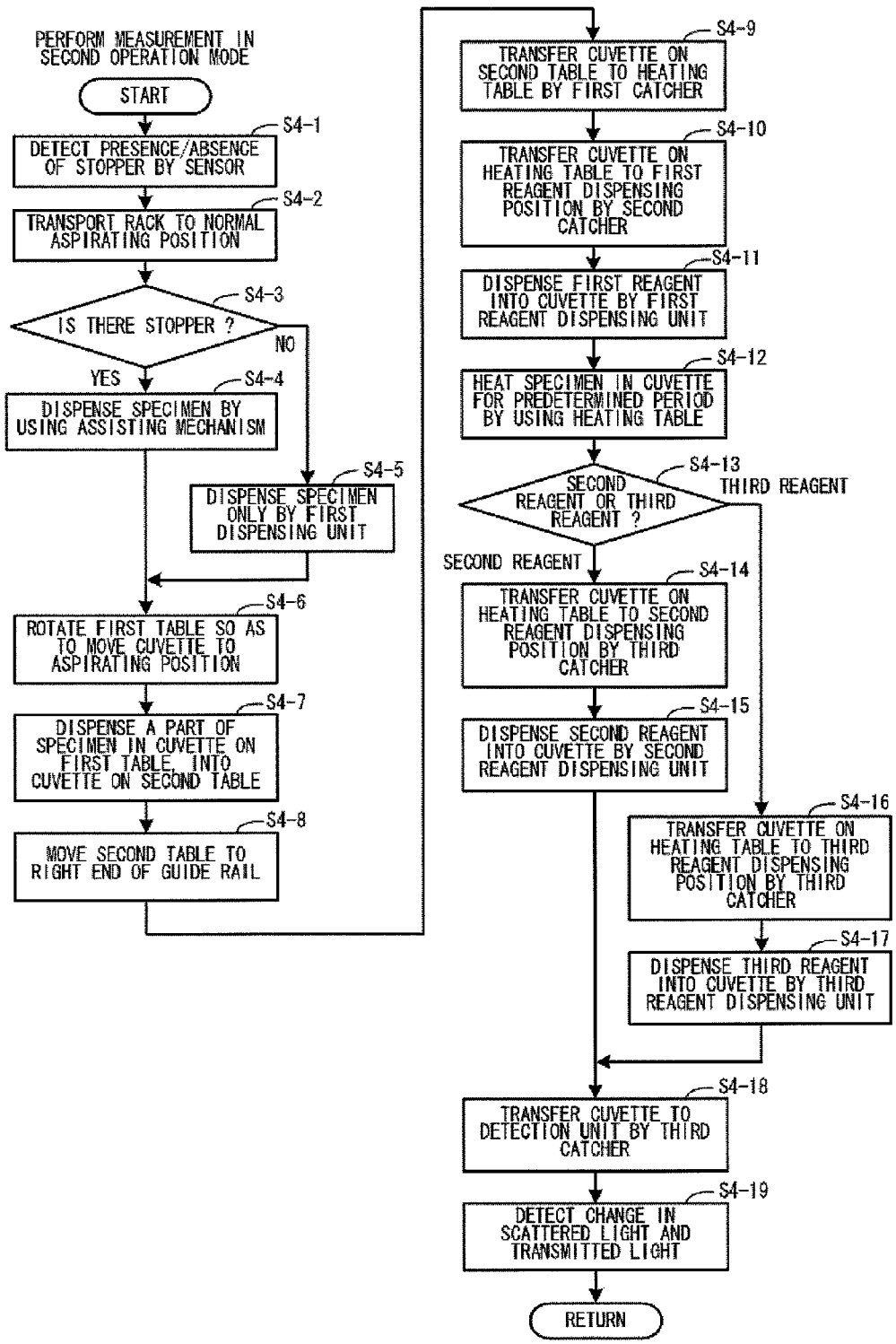
FIG. 13 is a flowchart showing a specimen measuring operation that is performed, in a second operation mode, by the measurement apparatus 2 according to the embodiment of the present invention.

FIG. 13 is a flowchart showing the specimen measuring operation in the second operation mode. Hereinafter, the specimen measuring operation in the second operation mode will be described with reference to FIG. 13.

At step S4-1, the CPU 200a confirms by means of the sensor unit 203 whether or not the stopper 403 is inserted into the specimen container 401, held by the rack 404, in the bar code read position 201c.

Next, at step S4-2, the CPU 200a controls the transporting unit 201 in order to transport the rack 404 to the aspirating position 201b.

Next, at step S4-3, the CPU 200a performs a process of determining, based on a result of the process at step S4-1, whether or not the stopper 403 is inserted into the specimen container 401. When it is determined that the stopper 403 is inserted into the specimen container 401 (YES at step S4-3), the CPU 200a performs, at step S4-4, a process of controlling the first dispensing unit 204 and the cuvette table 206c for specimen dispensing. First, the cuvette table 206c rotates, whereby a cuvette 217 is moved to the container position 206a. Next, the arm 204a rotates, whereby the pipette 204d is disposed above the aspirating position 201b. Next, the arm 204a and the engagement member 204f become engaged with each other, and a downward driving force of the driving section 204g causes the arm 204a and the pipette 204d to descend. At this point, the pipette 204d penetrates through the stopper 403 of the specimen container 401 in the aspirating position 201b. Next, the specimen is aspirated from the specimen container 401 by the pipette 204d and the pump. Next, an upward driving force of the driving section 204g causes the arm 204a and the pipette 204d to ascend. Subsequently, the arm 204a rotates, whereby the pipette 204d is disposed above the container position 206a. Then, the specimen is discharged into the cuvette 217 by the pipette 204d and the pump.

When the stopper 403 is not inserted into the specimen container 401 (NO at step S4-3), the CPU 200a controls, at step S4-5, the first dispensing unit 204 and the cuvette table 206c for specimen dispensing. First, the cuvette table 206c rotates, whereby a cuvette 217 is moved to the container position 206a. Next, the arm 204a rotates, whereby the pipette 204d is disposed above the aspirating position 201b. Subsequently, a downward driving force of the driving section 204b causes the arm 204a and the pipette 204d to descend. Then, the specimen in the specimen container 401 in the aspirating position 201b is aspirated by the pipette 204d and the pump. Next, an upward driving force of the driving section 204b causes the arm 204a and the pipette 204d to ascend. Subsequently, the arm 204a rotates, whereby the pipette 204d is disposed above the container position 206a. Then, the specimen is discharged into the cuvette 217 by the pipette 204d and the pump.

When the specimen is dispensed into the cuvette 217 in the container position 206a, the CPU 200a controls the cuvette table 206c at step S4-6 so as to move the cuvette 217, into which the first dispensing unit 204 has dispensed the specimen, to the container position 206b.

Next, at step S4-7, the CPU 200a controls the second dispensing unit 205 in order to dispense, from the cuvette 217 having been moved to the container position 206b, the specimen into a cuvette 217 held by the second table unit 207. First, the arm 205a rotates, whereby the pipette 205d is disposed above the container position 206b. Next, a downward driving force of the driving section 205b causes the arm 205a and the pipette 205d to descend. Subsequently, the specimen is aspirated from the cuvette 217 in the container position 206b by the pipette 205d and the pump, by a predetermined amount in accordance with a corresponding measurement item. At this point, the specimen remains in the cuvette 217 in the container position 206b, in a particular amount that allows the examination to be performed thereupon again. Next, the arm 205a rotates, whereby the pipette 205d is disposed above the cuvette 217 held by the second table unit 207. Then, the specimen is discharged into the cuvette 217 by the pipette 205d and the pump.

At this point, the CPU 200a controls the cuvette table 206c in order to move the cuvette 217 in the container position 206b to a different position (not shown) on the cuvette table 206c. This cuvette 217 is held by the cuvette table 206c until measurement of the same specimen as that contained therein is completed. Further, the CPU 200a controls the second catcher unit 211 so as to transfer a new cuvette 217 to the cuvette table 206c.

The processes at steps S4-8 to S4-19 are the same as those performed at steps S3-6 to S3-17. Therefore, the description thereof will be omitted. After performing the process at step S4-19, the CPU 200a performs the process at step S1-10.

Note that, if abnormality is found in the analysis result of the specimen measured in the second operation mode, the CPU 301a transmits, to the CPU 200a, an instruction to re-examine the specimen in which the abnormality has been observed. Upon receiving the re-examination instruction transmitted from the CPU 301a, the CPU 200a controls the cuvette table 206c so as to move the cuvette 217, which is held by the cuvette table 206c and which contains the partial specimen to be re-examined, to the container position 206b. Thereafter, the CPU 200a re-examines the specimen by performing the processes at steps S4-7 to S4-19.

As described above, the specimen analyzing apparatus 1 of the present embodiment is configured to measure a specimen that does not require re-examination later (i.e., a specimen for which a re-examination schedule is "NOT SCHEDULED"), in the first operation mode that does not cause the specimen to remain in the specimen analyzing apparatus, and measure a specimen which requires re-examination later (i.e., a specimen for which a re-examination schedule is "SCHEDULED"), in the second operation mode that causes the specimen to remain in the specimen analyzing apparatus. In other words, the specimen analyzing apparatus of the present embodiment is configured to be able to efficiently analyze specimens depending on differences, among the specimens, in examination requirements.

Note that, the embodiment disclosed herein is merely illustrative in all aspects and should not be recognized as being restrictive. The scope of the present invention is defined by the scope of the claims rather than by the description of the above embodiment, and includes meaning equivalent to the scope of the claims and all modifications within the scope.

In the above embodiment, the specimen analyzing apparatus is configured as a blood coagulation measuring apparatus. However, the present invention is not limited thereto. Alternatively, the specimen analyzing apparatus may be configured as an immunoanalyzer or a biochemical analyzer.

Further, in the above embodiment, the second dispensing unit 205 is configured to dispense the specimen from the specimen container 401 that has been transported by the transporting unit 201 to the aspirating position 201a, into the cuvette 217 held by the second table unit 207. The second dispensing unit 205 is also configured to dispense the specimen from the cuvette 217 which is in the container position 206b on the cuvette table 206c and into which the specimen has been dispensed by the first dispensing unit 204, into the cuvette 217 on the second table unit 207. However, the present invention is not limited thereto. Alternatively, the second dispensing unit 205 may be configured to dispense the specimen from the specimen container 401 into the cuvette 217 held by the second table unit 207, and a different dispensing unit from the first and second dispensing units 204 and 205 may be configured to dispense the specimen from the cuvette 217 on the cuvette table 206c into the cuvette 217 on the second table unit 207.

Still further, in the above embodiment, the first dispensing unit 204 dispenses the specimen by an amount necessary for performing the measurement a plurality of times, and the second dispensing unit 205 dispenses the specimen by an amount necessary for performing the measurement once. However, the present invention is not limited thereto. If the amount of specimen dispensed by the first dispensing unit 204 is less than the amount of specimen dispensed by the second dispensing unit 205, the second dispensing unit 205 may dispense the specimen by an amount necessary for performing the measurement a plurality of times.

Still further, in the above embodiment, the operator registers the measurement order with the host computer. However, the present invention is not limited thereto. The operator may register the measurement order with the information processing apparatus 3.

Still further, the above embodiment describes an example where the re-examination schedule is set for each specimen container 401. However, the present invention is not limited thereto. The re-examination schedule may be set for each rack 404.

Still further, in the above embodiment, the positions in which the first dispensing unit 204 and the second dispensing unit 205 aspirate the specimens from the specimen containers 401 are set to the specimen aspirating position 201b and the specimen aspirating position 201a, respectively, which are different from each other. However, the present invention is not limited thereto. The first dispensing unit 204 and the second dispensing unit 205 may aspirate the specimens from the specimen containers 401 at the same position.

Still further, in the above embodiment, the first dispensing unit 204 and the second dispensing unit 205 aspirate the specimens from the specimen containers 401 and discharge the specimens into the cuvettes 217, by means of the pipette 204d and the pipette 205d, respectively. In this manner, the specimens are supplied to the cuvettes 217. However, the present invention is not limited thereto. The pipettes included in the respective dispensing units may be detached therefrom, and may also be used as cuvettes.

Figure 16A:
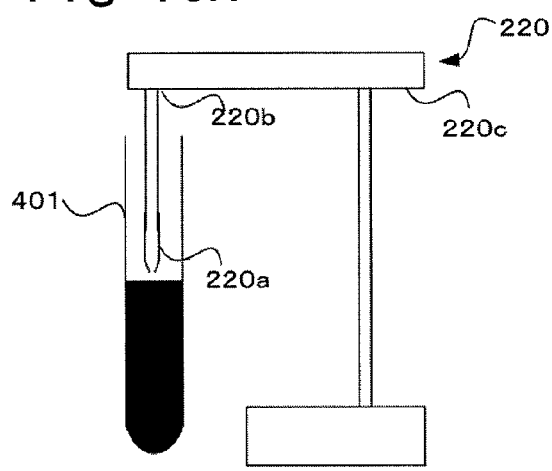
FIGS. 16A to 16D illustrate operations performed by a dispensing unit 220 according to another embodiment of the present invention.
Figure 16B:
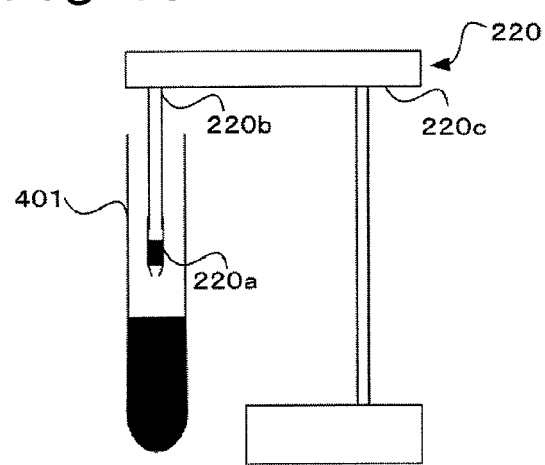
Figure 16C:
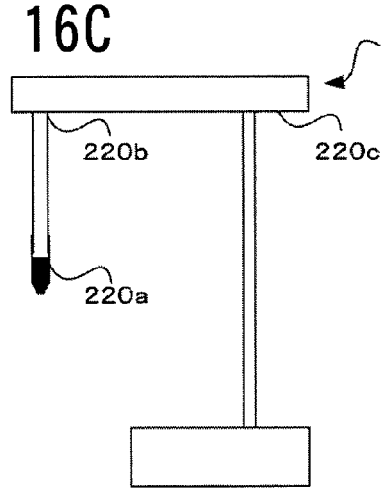
Figure 16D:
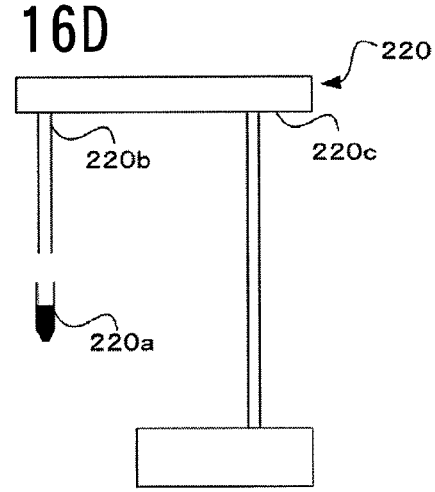

FIGS. 16A to 16D illustrate operations performed by a dispensing unit 220 in the aforementioned configuration. Hereinafter, the operations performed by the dispensing unit 220 in the above configuration will be described with reference to FIGS. 16A to 16D. As shown in FIG. 16A, the dispensing unit 220 includes an arm 220c provided with a shaft 220b for holding a pipette 220a. Here, the pipette 220a is configured to be detachable from the shaft 220b. First, as shown in FIG. 16B, a specimen is supplied to the pipette 220a when the specimen contained in the specimen container 401 is aspirated by a pump (not shown) included in the dispensing unit 220. Here, the measurement apparatus 2 includes a sealer (not shown) for heating the tip of the pipette 220a and thereby sealing the opening of the pipette 220a. When the specimen is supplied to the pipette 220a, the opening of the pipette 220a is sealed by the sealer as shown in FIG. 16C. Accordingly, the pipette 220a is used as a cuvette thereafter. Here, the measurement apparatus 2 includes a separator (not shown) for separating the pipette 220a from the shaft 220b. When the opening of the pipette 220a is sealed by the sealer, the pipette 220a is separated from the shaft 220b by the separator as shown in FIG. 16D, and transferred to the cuvette table 206c or to the second table unit 207. Then, the pipette 220a is transferred to the detection unit 216, and the specimen contained in the pipette 220a is measured.

Figure 17:
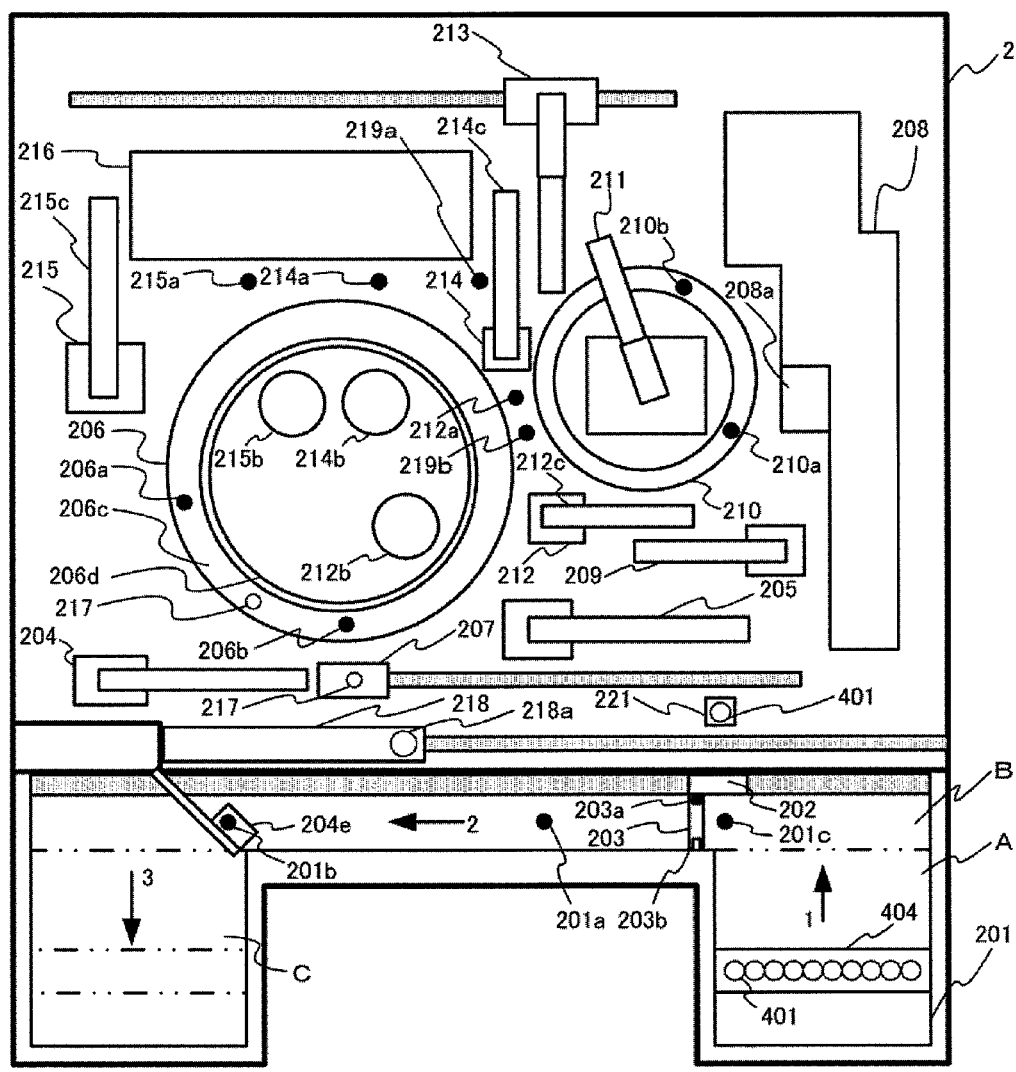
FIG. 17 is a schematic diagram showing a configuration of the measurement apparatus 2 that includes an interruption specimen setting section 221 according to another embodiment of the present invention.

Still further, the measurement apparatus 2 may include an interruption specimen setting section for setting therein a specimen container 401 that contains a specimen to be preferentially analyzed. FIG. 17 is a schematic diagram showing a configuration of the measurement apparatus 2 including an interruption specimen setting section 221. As shown in FIG. 17, when a specimen container 401 is set into the interruption specimen setting section 221, the CPU 200a interrupts, at the time, the aspirating of the specimen from the specimen containers 401 held by the rack 404, and performs a process of controlling the second dispensing unit 205 so as to dispense, from the specimen container 401 set in the interruption specimen setting section 221, the specimen into the cuvette 217 on the second table unit 207. Thereafter, the CPU 200a performs the processes at steps S3-6 to S3-17.

Still further, in the above embodiment, the CPU 200a selects, based on the presence or absence of the re-examination schedule in the measurement order, whether to perform the measurement in the first operation mode or to perform the measurement in the second operation mode. However, the present invention is not limited thereto. Which operation mode is selected for performing the measurement may be determined based on other conditions.

For example, information indicating whether or not the stopper 403 is inserted into the specimen container 401 may be contained in the measurement order, and based on the information, the CPU 200a may select either one of the operation modes for the measurement. Here, the CPU 200a controls the measurement apparatus 2 so as to perform the measurement in the first operation mode when the stopper 403 is not inserted into the specimen container 401, and to perform the measurement in the second operation mode when the stopper 403 is inserted into the specimen container 401. In this manner, a predetermined amount of specimen can be immediately aspirated from the specimen container 401 into which the stopper 403 is not inserted. Note that, also in the case of the specimen contained in the specimen container 401 having the stopper 403 inserted thereinto (e.g., a vacuum blood collection tube), the first dispensing unit 204 dispenses the specimen from the specimen container 401 into a cuvette by a greater amount than an amount necessary for performing the measurement once, and thereafter the specimen is aspirated from the cuvette by the second dispensing unit 205 by a predetermined amount. Accordingly, when aspirating a predetermined amount of specimen from the specimen container having the stopper 403 inserted thereinto, it is no longer necessary to perform a complex operation in which, for example, the measurement apparatus 2 pierces the stopper 403 by using a piercer (not shown) to release pressure from the inside of the specimen container having the stopper 403 inserted thereinto, and then aspirates the specimen therefrom via the pipette 205d and the pump (not shown) of the second dispensing unit 205. Therefore, even if a specimen container 401 having the stopper 403 inserted thereinto and a specimen container 401 not having the stopper 403 inserted thereinto are mixed, the examination can be performed speedily.

Further, information about the amount of specimen contained in the specimen container 401 may be included in the measurement order, and based on the information, the CPU 200a may select either one of the operation modes for the measurement. Here, the CPU 200a controls the measurement apparatus 2 so as to perform the measurement in the second operation mode when the specimen contained in the specimen container 401 is a predetermined amount or more, and to perform the measurement in the first operation mode when the specimen contained in the specimen container 401 is less than the predetermined amount. Note that, a necessary amount of specimen for each measurement item is stored in the ROM 200e. For example, when the amount of specimen contained in the specimen container 401 is insufficient to perform the measurement once, the CPU 200a controls the measurement apparatus 2 in order to perform the measurement in the first operation mode. Further, even in the case where the re-examination schedule is set for the specimen contained in the specimen container 401, if the amount of specimen contained in the specimen container 401 is insufficient to perform the measurement twice, then the CPU 200a controls the measurement apparatus 2 so as to perform the measurement in the first operation mode. In this manner, examination can be performed speedily even if the specimen contained in the specimen container 401 is a specimen of a small amount such as an infantile specimen, or is a specimen that does not allow re-examination thereupon due to its insufficient amount.

Still further, in the above embodiment, the CPU 301a of the information processing apparatus 3 analyzes the specimen measurement results transmitted from the CPU 200a of the measurement apparatus 2. However, the present invention is not limited thereto. The analysis program 307 may be stored in the ROM 200e, and the CPU 200a may perform a process of analyzing the specimen measurement results by executing the analysis program 307. In this case, the CPU 200a causes the RAM 200c to store the specimen measurement results obtained through the first operation mode or the second operation mode. Next, the CPU 200a executes the analysis program 307 stored in the ROM 200e, thereby analyzing the measurement results. Then, the CPU 200a causes the RAM 200c to store a result obtained from the analysis. Subsequently, the CPU 200a transmits the analysis result stored in the RAM 200c to the information processing apparatus 3 via the communication interface 200d. Then, the CPU 301a receives the analysis result transmitted from the measurement apparatus 2, and causes the hard disk 301d to store the received analysis result and causes the display section 302 to display the analysis result.

What is claimed is:

1. A specimen analyzing apparatus comprising:
   a detector for detecting component information regarding a component in a specimen contained in each of analyzing containers, the analyzing containers comprising first and second analyzing containers;
   an analyzing part for analyzing the component information detected by the detector;
   a transporting device for transporting specimen containers each containing a specimen, the specimen containers comprising first and second specimen containers;
   an operation mode selector for selecting one of a first operation mode for supplying the specimen of a first amount, which is a necessary amount for analyzing the specimen, from the first specimen container to the first analyzing container, and a second operation mode for supplying the specimen of a second amount greater than the first amount from the second specimen container to a reserve container and for supplying the specimen of the first amount from the reserve container to the second analyzing container;
   a first supplying device for supplying the specimen of the first amount;
   a second supplying device for supplying the specimen of the second amount; and
   a supply controller for controlling the first and second supplying devices in accordance with an operation mode selected by the operation mode selector.

2. The specimen analyzing apparatus of claim 1, wherein the supply controller controls the first and second supplying devices such that the first supplying device supplies the specimen of the first amount from the first specimen container to the first analyzing container when the operation mode selector has selected the first operation mode, and the second supplying device supplies the specimen of the second amount from the second specimen container to the reserve container when the operation mode selector has selected the second operation mode.

3. The specimen analyzing apparatus of claim 1, wherein the supply controller controls the first and second supplying devices such that the second supplying device supplies the specimen of the second amount from the second specimen container to the reserve container, and the first supplying device supplies the specimen of the first amount from the reserve container to the second analyzing container, when the operation mode selector has selected the second operation mode.

4. The specimen analyzing apparatus of claim 1, wherein the reserve container and the first and second analyzing containers have the same shape.

5. The specimen analyzing apparatus of claim 1, wherein the first supplying device comprises a liquid aspirating tube having a flat surface formed at a tip thereof, the flat surface having a liquid aspirating aperture.

6. The specimen analyzing apparatus of claim 1, wherein the second supplying device comprises a liquid aspirating tube which is formed so as to be able to penetrate through a lid covering an opening of the specimen container.

7. The specimen analyzing apparatus of claim 1, wherein
the operation mode selector selects the first operation mode with respect to a specimen container when an opening thereof is not covered by a lid and selects the second operation mode with respect to a specimen container when an opening thereof is covered by a lid.

8. The specimen analyzing apparatus of claim 1, wherein
the operation mode selector selects the first operation mode with respect to a specimen container containing a specimen to which a re-examination is not to be automatically performed, and selects the second operation mode with respect to a specimen container containing a specimen to which the re-examination is to be automatically performed depending on analysis result by the analyzing part.

9. The specimen analyzing apparatus of claim 8, wherein
the second amount is a necessary amount for examining the specimen a plurality of times.

10. The specimen analyzing apparatus of claim 1, wherein
the operation mode selector selects the first operation mode with respect to a specimen container containing a specimen of an amount less than a predetermined amount.

11. The specimen analyzing apparatus of claim 1, further comprising
an interruption specimen holder for holding an interruption specimen container which contains an interruption specimen, wherein
the operation mode selector automatically selects the first operation mode after the interruption specimen container has been held by the interruption specimen holder, and
the supply controller controls the first supplying device so as to supply the interruption specimen of the first amount from the interruption specimen container held by the interruption specimen holder to the first analyzing container.

12. A specimen analyzing apparatus comprising:
a detector for detecting component information regarding a component in a specimen contained in each of analyzing containers, the analyzing containers comprising first and second analyzing containers;
an information analyzing device for analyzing the component information detected by the detector;
a first supplying device for supplying the specimen of a first amount that is a necessary amount for the analyzing by the information analyzing device;
a second supplying device for supplying the specimen of a second amount that is greater than the first amount;
a transporting device for transporting specimen containers each containing a specimen, the specimen containers comprising first and second specimen containers; and
a control device for performing a process comprising:
(a) selecting one of a first operation mode for supplying the specimen of the first amount from the first specimen container to the first analyzing container, and a second operation mode for supplying the specimen of the second amount from the second specimen container to a reserve container and for supplying the specimen of the first amount from the reserve container to the second analyzing container; and
(b) controlling the first and second supplying devices in accordance with the selected operation mode.

13. The specimen analyzing apparatus of claim 12, wherein
the control device controls the first and second supplying devices such that the first supplying device supplies the specimen of the first amount from the first specimen container to the first analyzing container when the first operation mode has been selected, and the second supplying device supplies the specimen of the second amount from the second specimen container to the reserve container when the second operation mode has been selected.

14. The specimen analyzing apparatus of claim 12, wherein
the control device controls the first and second supplying devices such that the second supplying device supplies the specimen of the second amount from the second specimen container to the reserve container, and the first supplying device supplies the specimen of the first amount from the reserve container to the second analyzing container, when the second operation mode has been selected.

15. A specimen analyzing method comprising steps of:
(a) transporting specimen containers each containing a specimen, the specimen containers comprising first and second specimen containers;
(b) selecting one of a first operation mode and a second operation mode;
(c) supplying the specimen of a first amount which is a necessary amount for analyzing the specimen, from the first specimen container to a first analyzing container when the first operation mode has been selected;
(d) supplying the specimen of a second amount which is greater than the first amount, from the second specimen container to a reserve container, and supplying the specimen of the first amount from the reserve container to a second analyzing container when the second operation mode has been selected;
(e) detecting component information regarding a component contained in the specimen having been supplied to the first or second analyzing container; and
(f) analyzing the component information.

16. The specimen analyzing method of claim 15, wherein the step (b) comprises:
selecting the first operation mode with respect to a specimen container when an opening thereof is not covered by a lid; and
selecting the second operation mode with respect to a specimen container when an opening thereof is covered by a lid.

17. The specimen analyzing method of claim 15, wherein the step (b) comprises:
selecting the first operation mode with respect to a specimen container containing a specimen to which a re-examination is not to be automatically performed; and
selecting the second operation mode with respect to a specimen container containing a specimen to which the re-examination is to be automatically performed depending on analysis result at the step (f).

18. The specimen analyzing method of claim 17, wherein the second amount is a necessary amount for examining the specimen a plurality of times.

19. The specimen analyzing method of claim 15, wherein the step (b) comprises selecting the first operation mode with respect to a specimen container containing a specimen of an amount less than a predetermined amount.

* * * * *